US012240892B2

United States Patent
Park et al.

(10) Patent No.: US 12,240,892 B2
(45) Date of Patent: Mar. 4, 2025

(54) PHARMACEUTICAL COMPOSITION COMPRISING EXPRESSION OR ACTIVITY INHIBITOR OF C-SRC FOR PREVENTING OR TREATING SYNUCLEINOPATHY

(71) Applicant: AJOU UNIVERSITY INDUSTRY-ACADEMIC COOPERATION FOUNDATION, Suwon-si (KR)

(72) Inventors: Sang Myun Park, Suwon-si (KR); Yu Ree Choi, Suwon-si (KR); Jae Bong Kim, Busan (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 971 days.

(21) Appl. No.: 17/113,630

(22) Filed: Dec. 7, 2020

(65) Prior Publication Data

US 2021/0101966 A1    Apr. 8, 2021

Related U.S. Application Data

(63) Continuation-in-part of application No. PCT/KR2019/006870, filed on Jun. 7, 2019.

(30) Foreign Application Priority Data

Jun. 8, 2018   (KR) .......................... 10-2018-0066005

(51) Int. Cl.
*C07K 16/18*    (2006.01)
*A61K 39/00*    (2006.01)
(Continued)

(52) U.S. Cl.
CPC .............. *C07K 16/18* (2013.01); *A61K 39/00* (2013.01); *A61P 25/28* (2018.01); *C12N 15/113* (2013.01); *A61K 2039/505* (2013.01)

(58) Field of Classification Search
CPC ....... C07K 16/18; A61P 25/28; C12N 15/113; A61K 2039/505
See application file for complete search history.

(56) References Cited

U.S. PATENT DOCUMENTS 8,618,063 B2 *  12/2013  Brady ................... A61K 31/404
                                                514/17.7
10,085,976 B2 * 10/2018  Park .................... A61K 31/7105
(Continued)

FOREIGN PATENT DOCUMENTS

GB        2465308 A    5/2010
KR    10-1838802 A     1/2017

OTHER PUBLICATIONS

Clinic, Mayo, "Parkinson's disease", Mayo Clinic. https://www.mayoclinic.org/diseases-conditions/parkinsons-disease/symptoms-causes/syc-20376055#:~:text=Prevention,the%20risk%20of%20Parkinson's%20disease. (Year: 2023).*
(Continued)

*Primary Examiner* — Aurora M Fontainhas
*Assistant Examiner* — Selam Berhane
(74) *Attorney, Agent, or Firm* — Sughrue Mion, PLLC

(57) ABSTRACT

A composition including a substance that inhibits an expression or activity of c-src and its use in inhibiting aggregation and/or migration of α-syn are disclosed. The composition may be a pharmaceutical composition and can be used for preventing or treating synucleinopathy. The substance can inhibit the signal transduction induced by α-syn migrating to adjacent cells, thus mitigating the cytotoxic influence of α-syn on the adjacent cells; and can inhibit the denaturation of monomeric α-syn into aggregated α-syn, which may be (Continued)

a major cause of synucleinopathy, and thus, can be beneficially used as a therapeutic agent for synucleinopathy.

**3 Claims, 21 Drawing Sheets
(11 of 21 Drawing Sheet(s) Filed in Color)
Specification includes a Sequence Listing.**

(51) Int. Cl.
*A61P 25/28* (2006.01)
*C12N 15/113* (2010.01)

(56) References Cited

U.S. PATENT DOCUMENTS

| | | | |
|---|---|---|---|
| 2009/0258814 A1 | 10/2009 | Brady et al. | |
| 2014/0371233 A1* | 12/2014 | Strittmatter | A61K 31/517 544/283 |
| 2017/0143686 A1* | 5/2017 | Choi | G01N 33/5058 |
| 2023/0013435 A1* | 1/2023 | Park | A61K 9/0053 |
| 2023/0017675 A1* | 1/2023 | Park | A61P 25/16 |

OTHER PUBLICATIONS

Kang et al., "a-Synuclein binds and sequesters PIKE-L into Lewy bodies, triggering dopaminergic cell death via AMPK hyperactivation", PNAS, Jan. 31, 2017, pp. 1183-1188, vol. 114, No. 5.
He Yixin et al., "Mechanism of a-syn aggregation and dissemination in synucleinopathy", Chinese Journal of Practical Nervous Diseases, Febuary, 2016, vol. 19, pp. 77-79, No. 4.
Chinese Office Action dated Oct. 19, 2022 in Chinese Application No. 201980046255.2.
Search Report dated Oct. 12, 2022 for the CN patent application No. 201980046255.2.
Raghvendra Singh, et al., "PKC-δ binds to E-cadherin and mediates EGF-induced cell scattering", Elsevier Inc, Experimental Cell Research, vol. 315, 2009, pp. 2899-2913 (15 pages).
Chinese Office Action dated Aug. 30, 2023 in CN Appln No. 201980046255.2.
Savita Khanna, et al., "Regulation of c-Src Activity in Glutamate-induced Neurodegeneration", The Journal of Biological Chemistry, Aug. 10, 2007, pp. 23482-23490, vol. 282, No. 32.
Sun Young Park, et al., "Neuroprotective effects of a-iso-cubebene against glutamate-induced damage in the HT22 hippocampal neuronal cell line", International Journal of Molecular Medicine, 2015, pp. 525-532, vol. 35.
Eun Joo Kim, et al., "Dyrk 1A Phosphorylates a-Synuclein and Enhances Intracellular Inclusion Formation", The Journal of Biological Chemistry, Nov. 3, 2006, pp. 33250-33257, vol. 281, No. 44.
Christopher E. Ellis, et al., "a-Synuclein Is Phosphorylated by Members of the Src Family of Protein-tyrosine Kinases", The Journal of Biological Chemistry, Feb. 9, 2001, pp. 3879-3884, vol. 276, No. 6.
Takeshi Nakamura, et al., "Activation of Pyk2/RAFTK induces tyrosine phosphorylation of a-synuclein via Src-family kinases", FEBS Letters., 2002, pp. 190-194, vol. 521.
Dr. Fatemeh Nouri Emamzadeh, "Alpha-synuclein structure, functions, and interactions", Alpha-synuclein structure, functions, and interactions, 2016, pp. 1-9, vol. 21, No. 29.
Andrew J. Lees, et al., "Parkinson's disease", Seminar, 2009, pp. 2055-2066, vol. 373.
Judith Eschbach, et al., "a-Synuclein in Parkinson's Disease: Pathogenic Function and Translation into Animal Models", Review, Neurodegener Dis, 2013, vol. 14, pp. 1-17.
Maddalena Costanzo, et al., "The cell biology of prison-like spread of protein aggregates: mechanisms and implication in neurodegeneration", Biochem J., 2013, pp. 1-17, vol. 452.
Michel Goedert, et al., "The propagation of prion-like protein inclusions in neurodegenerative diseases", Trends in Neurosciences, 2010, pp. 317-325, vol. 33.
Seung-Jae Lee, et al., "Pathological Propagation through Cell-to-Cell Transmission of Non-Prion Protein Aggregates in Neurodegenerative Disorders", Nat. Rev. Neurol. Dec. 2010, pp. 702-706.
Saet-Byul Lee, et al., "Identification of the amino acid sequence motif of a-synuclein responsible for macrophage activation", Biochemical and Biophysical Research Communications, 2009, pp. 39-43.
S. Yoon, et al., "Caspase-dependent cell death-associated release of nucleosome and damage-associated molecular patterns", Cell Death and Disease, 2014, e1494.
Seon-Heui Cha, et al., "Loss of parkin promotes lipid rafts-dependent endocytosis through accumulating caveolin-1: implications for Parkinson's disease", Molecular Neurodegeneration, pp. 2015, vol. 10, No. 63.
He-Jin Lee, et al., "Transmission of Synucleinopathies in the Enteric Nervous System of A53T Alpha-Synuclein Transgenic Mice", Experimental Neurobiology, Dec. 20, 2011, pp. 181-188, vol. 4.
International Searching Authority, International Search Report for PCT/KR2019/006870 dated Sep. 5, 2019 [PCT/ISA/210].
International Searching Authority, Written Opinion for PCT/KR2019/006870 dated Sep. 5, 2019 [PCT/ISA/237].
Korea Intellectual Property Office, Korean Office Action 10-2019-0067253 (priority KR 10-2018-0066005) Oct. 14, 2020.

* cited by examiner

SH-SY5Y

Primary Neurons

SHP-1 KD SHSY5Y

C-src KD SHSY5Y

Differentiated SH-SY5Y

Differentiated SH-SY5Y

ID
PHARMACEUTICAL COMPOSITION COMPRISING EXPRESSION OR ACTIVITY INHIBITOR OF C-SRC FOR PREVENTING OR TREATING SYNUCLEINOPATHY

CROSS REFERENCE TO RELATED APPLICATIONS

This application is a continuation-in-part application of PCT/KR2019/006870 filed Jun. 7, 2019, which claims priority from Korean Patent Application No. 10-2018-0066005 filed Jun. 8, 2018.

TECHNICAL FIELD

The present invention relates to a composition for inhibiting the aggregation and/or migration of alpha-synuclein ($\alpha$-synuclein; $\alpha$-syn), and more specifically to a composition comprising an inhibitor for expression or activation of c-src, and its use in preventing or treating synucleinopathy comprising an inhibitor for expression or activation of c-src.

BACKGROUND ART

As the size of the aging population increases, the number of patients suffering from degenerative brain diseases such as Parkinson's disease and Alzheimer's disease is rapidly increasing, and medical costs to solve this problem are also rapidly increasing. Among degenerative brain diseases, Parkinson's disease is the second most common degenerative brain disease after Alzheimer's disease, and is the most common degenerative motor disease. The number of patients suffering from the disease is estimated to be more than 1% of all persons over 60 years of age worldwide, and the number of patients in Korea increased continually from 40,000 in 2004 to 66,000 in 2008 and 93,000 in 2012, and is expected to increase even more rapidly in the future.

The exact cause of Parkinson's disease is still unknown, but familial Parkinson's disease is known to be caused by various genetic mutations involving, for example, $\alpha$-synuclein, parkin, PINK1, DJ-1, and LRRK2. In addition, as far as is known, it is inferred that Parkinson's disease is caused by oxidative stress, mitochondrial abnormalities, and problems in cellular protein removal function (Lees, A J, et al, Lancet, 373:2055-66, 2009), and is caused by environmental influences along with genetic factors. The onset of Parkinson's disease is detected based on clinical symptoms, and treatment is limited to conservative treatment that alleviates symptoms rather than eliminates the cause. Therefore, it is an urgent issue to accurately identify the etiology and find a therapy method suitable therefor.

Alpha-synuclein ($\alpha$-synuclein; $\alpha$-syn) is a major constituent protein of the Lewy body in the cytoplasm found in patients of Parkinson's disease, is mainly distributed at the end of the presynapse of nerve cells, and is known to be expressed in large amounts in overall nerve tissues. Alpha-synuclein is also involved in the pathogenesis of other degenerative diseases such as dementia with Lewy bodies and multiple system atrophy, as well as Parkinson's disease. All diseases associated with abnormal accumulation of alpha-synuclein are collectively referred to as "synucleinopathy", and a great deal of research is actively conducted on alpha-synuclein as a common therapeutic target for the diseases.

In addition, alpha-synuclein has the ability to form an aggregate, and the possibility that the denaturation process in which the monomeric alpha-synuclein is converted to aggregated alpha-synuclein could be the main cause of Parkinson's disease was made known (Eschbach, J., Danzer, K. M., *Neurodegener. Dis.*, 14:1-17, 2013), after which duplication and triplication of the gene were identified in familial Parkinson's disease, so efforts to find the functions of alpha-synuclein have been more intensively made. As a pharmaceutical composition targeting the aggregated alpha-synuclein according thereto, a pharmaceutical composition for treating Parkinson's disease containing, as an active ingredient, a Longan Arillus extract that can significantly protect dopaminergic neurons from neurotoxicity caused by the aggregation of alpha-synuclein has been developed (Korean Patent No. 1189191). However, the specific receptors on which alpha-synuclein acts and the mechanisms related thereto have not been elucidated yet.

Meanwhile, the denaturation process in which protein monomers are converted into aggregates occurs not only in alpha-synuclein of Parkinson's disease, but also in amyloid beta (A$\beta$) of Alzheimer's disease, tau, mutated huntingtin of Huntington's disease, and the prion of prion disease, and this degeneration process is considered to be a common cause of many degenerative brain diseases, and research is actively being conducted on the treatment of degenerative brain diseases by suppressing this process.

Since then, interest in the possibility of intracellular delivery of alpha-synuclein has rapidly increased, and the possibility that aggregated alpha-synuclein also enters adjacent cells and is involved in the production of Lewy bodies and apoptosis of the adjacent cells has been gradually revealed, for example, prion of prion disease combines with normal prion expressed in normal neurons to form an aggregate (Costanzo, M., Zurzolo, C., Biochem. J. 452:1-17, 2013; Goedert, M. et al., *Trends Neurosci.* 33:317-25, 2010; Lee, S. J., et al., *Nat. Rev. Neurol.* 6:702-6, 2010). When inferring the pathogenesis of Parkinson's disease caused by alpha-synuclein located outside the cell from this, various types of alpha-synuclein secreted from the cell are involved in neurocytotoxicity by acting on and activating adjacent glial cells, and the neurocytotoxicity is expressed as direct toxicity through migration (metastasis) to adjacent neurons or as a series of cytotoxicity by inducing the development of Lewy bodies.

Therefore, receptors or constructions involved in the intracellular signaling process by alpha-synuclein located outside the cell can be an important clue for revealing the pathogenesis of many types of degenerative brain diseases. In addition, great interest is warranted because such receptors or constructions can be used to establish a novel treatment strategy different from that of the past, but research related thereto has not been actively conducted.

Accordingly, as a result of intensive research efforts to identify the mechanism of action by which alpha-synuclein migrates into adjacent cells, the present inventors confirmed that the activation of c-src is involved in the aggregate formation and migration of alpha-synuclein, and confirmed that synucleinopathy caused by alpha-synuclein, specifically degenerative brain diseases such as Parkinson's disease, dementia with Lewy bodies (DLB) or multiple system atrophy (MSA), can be prevented and treated by suppressing expression or activation of c-src, thereby completing the present invention.

The information disclosed in this Background section is provided only for enhancement of understanding of the background of the present invention, and therefore it may not include information that forms the prior art that is already obvious to those skilled in the art.

SUMMARY OF THE INVENTION

It is an object of the present invention to provide a composition for inhibiting aggregation and/or migration of α-synuclein (α-Syn), comprising an inhibitor for expression or activation of c-src protein capable of inhibiting the migration of α-syn to adjacent cells and the denaturation of an α-syn monomer into an α-syn aggregate.

It is another object of the present invention to provide a pharmaceutical composition for preventing or treating synucleinopathy comprising an inhibitor for expression or activation of c-src.

It is a further object of the present invention to provide a method of screening a therapeutic agent for synucleinopathy comprising measuring the level of expression or activation of a c-src protein in cells treated with a candidate substance for a therapeutic agent for synucleinopathy.

It is a further object of the present invention to provide a composition for diagnosing synucleinopathy comprising a substance capable of measuring an activation level of c-src, a kit for diagnosing synucleinopathy comprising the composition for diagnosis, and a method of providing information for diagnosing synucleinopathy, comprising measuring the level of activation of c-src using the composition or the kit.

To achieve the above object, an aspect of the present invention provides a composition for inhibiting aggregation and/or migration of α-synuclein (α-Syn) comprising an inhibitor for expression or activation of a c-src protein.

To achieve the above object, an aspect of the present invention provides a method of inhibiting aggregation and/or migration of α-synuclein (α-Syn), comprising administering the inhibitor for expression or activation of the c-src protein to a subject.

Another aspect of the present invention also provides a pharmaceutical composition for preventing or treating synucleinopathy comprising the inhibitor for expression or activation of c-src.

Still another aspect of the present invention also provides a method of treating synucleinopathy comprising administering the inhibitor for expression or activation of c-src to a subject.

An aspect of the present invention also provides a use of the inhibitor for expression or activation of c-src for the treatment of synucleinopathy and a use of the inhibitor for expression or activation of c-src for the preparation of a therapeutic agent for synucleinopathy.

An aspect of the present invention also provides a method of screening a therapeutic agent for synucleinopathy, the method comprising (i) treating a nerve-tissue-derived cell with a candidate substance for a therapeutic agent for synucleinopathy, (ii) measuring the level of expression or activation of c-src protein in the cell, and (iii) selecting a candidate substance that has a reduced expression or activation level of the c-src protein compared to a control group not treated with the candidate substance.

Another aspect of the present invention also provides a composition for diagnosing synucleinopathy comprising a substance capable of measuring the activation level of c-src.

Still another aspect of present invention also provides a kit for diagnosing synucleinopathy comprising the composition for diagnosis.

Another aspect of the present invention also provides a method of providing information for diagnosing synucleinopathy and a method of diagnosing synucleinopathy, each method comprising measuring the activation level of c-src in a biological sample isolated from a subject suspected of synucleinopathy using the composition or the kit.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION AND EMBODIMENTS

Figure 1A:
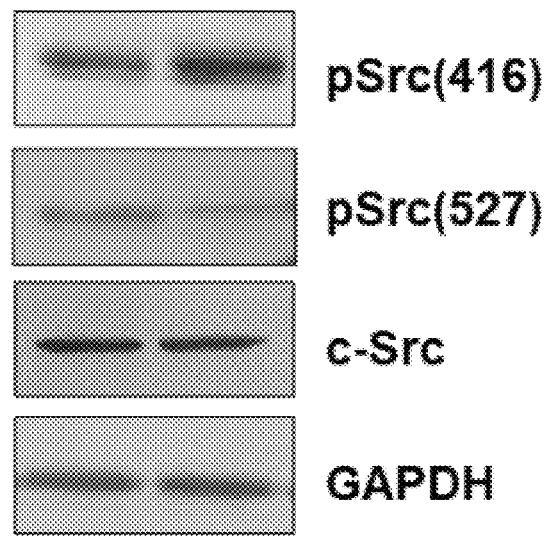
FIGS. 1A-1C show that the activation of c-src is increased by the aggregated α-syn in (FIG. 1A) a SHSY5Y cell line, in (FIG. 1B) mouse primary neurons, wherein $P<0.01$ represents the result compared to PBS, and in (FIG. 1C) whole brain lysates of wild-type mice and A53T TG mice, wherein $P<0.01$ represents the result compared to wild-type mice (WT).
Figure 1A:
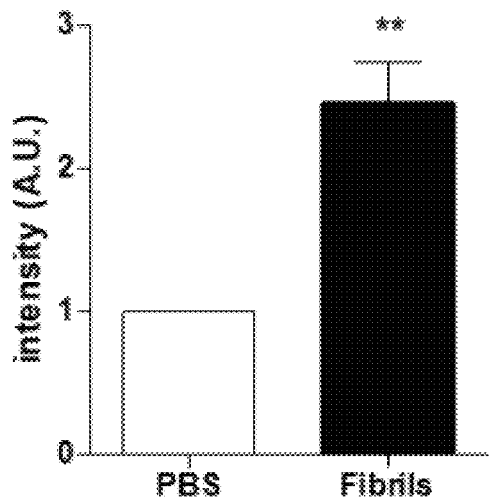
Figure 1A:
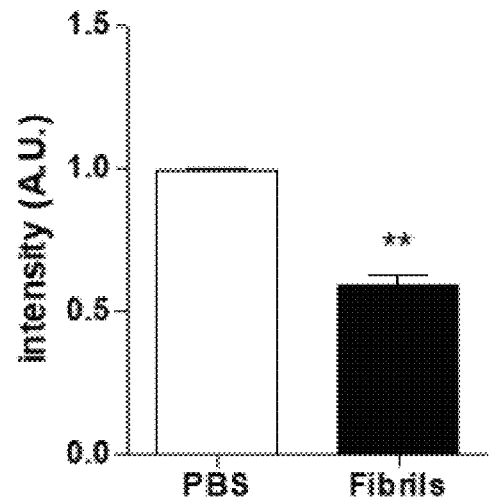

Unless defined otherwise, all technical and scientific terms used herein have the same meanings as appreciated by those skilled in the field to which the present invention pertains. In general, the nomenclature used herein is well-known in the art and is ordinarily used.

During various studies to establish a new and more effective treatment strategy by identifying the pathogenesis of degenerative brain diseases, the present inventors paid attention to alpha-synuclein (α-syn). Based on the possibility that alpha-synuclein secreted from nerve cells acts on adjacent neurons to activate the nerve cells and thereby cause damage to the nerve cells, the protein c-src is found to be involved in the invasion of aggregated alpha-synuclein outside cells into adjacent cells. In addition, it was confirmed that the c-src is also involved in the denaturation of α-syn to an aggregate, which may be a major cause of Parkinson's disease.

The present inventors found that the activation of c-src is improved by the aggregated α-syn, and the improved activation of c-src by α-syn is inhibited when the expression of SHP-1 or SHP-2 is inhibited. Furthermore, it was found that, when the expression of c-src was inhibited, intercellular migration of α-syn is reduced, which means that c-src plays an essential role in the migration of aggregated α-syn. In addition, it was found that c-src is involved in the process of denaturation to form the α-syn aggregate, which indicates that the degeneration of α-syn into aggregates, which is the main cause of synucleinopathy, can be suppressed by inhibition of c-src activation.

As such, the mechanism of migration of aggregated α-syn to adjacent cells and the mechanism of denaturation of monomeric α-syn into aggregated α-syn, which are important clues for revealing the cause of synucleinopathy, are not known at all in the prior art, and were first identified by the present inventors.

Therefore, in one aspect, the present invention is directed to a composition for inhibiting aggregation and/or migration of α-synuclein (α-Syn), comprising an inhibitor for expression or activation of a c-src protein.

In another aspect, the present invention is directed to a method of inhibiting aggregation and/or migration of α-synuclein (α-Syn), comprising administering an inhibitor for expression or activation of a c-src protein to a subject.

As used herein, the term "c-src" refers to a non-receptor tyrosine kinase protein encoded by a src gene, which is also known as proto-oncogene tyrosine-protein kinase Src or proto-oncogene c-src. The c-src phosphorylates certain tyrosine residues in other proteins. "c-src" is the abbreviation for cellular Src kinase. The increased activation level of c-src tyrosine kinase is known to be associated with cancer progression by promoting other signals. This oncogene can also play a role in the regulation of embryonic development and cell growth. c-src includes the SH2 domain, the SH3 domain, and the tyrosine kinase domain.

In the present invention, the gene sequence of the c-src protein can be obtained from a known database such as GenBank of NCBI, and, for example, may be the gene represented by GenBank Accession No. AAC29427.1.

As used herein, the term "c-src activation" means phosphorylation of c-src, which may be achieved by aggregated alpha-synuclein (α-synuclein; α-syn) based on the object of the present invention, and the c-src activation may be involved in the phenomenon of improving the migration of α-syn.

As used herein, the term "alpha-synuclein (α-synuclein; α-syn)" means a protein known as a major component of the Lewy body in the cytoplasm, but is not limited thereto, and may mean a protein molecule involved in the pathogenesis of degenerative brain disease based on the objects of the present invention. The nucleotide sequence of the α-syn gene can be obtained from a known database such as GenBank of NCBI, and may be, for example, a gene represented by GenBank Accession No. NP 0010359161.

As used herein, the term "migration of alpha-synuclein" refers to a phenomenon in which alpha-synuclein moves from a cell secreting alpha-synuclein to another cell located nearby. Although not limited thereto, it may be a phenomenon of exhibiting direct toxicity to adjacent cells or transferring of a signal exhibiting cytotoxicity into adjacent cells, and alpha synuclein migration can be activated by activation of c-src, based on the objects of the present invention. That is, when the aggregated alpha synuclein exists outside the cell, the activation of src is improved, and the alpha synuclein existing outside the cell enters the cell.

As used herein, the term "SHP-1/-2" refers to Src homology region 2 domain-containing phosphatase-1/-2, which is also known as PTPN6 (tyrosine-protein phosphatase non-receptor type 6) and is a kind of protein tyrosine phosphatase. The SHP-1/-2 includes a Src homolog (SH2) domain that acts as a protein phosphorylation-tyrosine binding domain at the N-terminus and is known as a signaling molecule that regulates various intercellular processes such as cell growth, differentiation and mitotic cycles. The gene sequence of the SHP-1/-2 protein can be obtained from a known database such as GenBank of NCBI. For example, it may be a gene represented by GenBank Accession No. AAC360091, AAC360081, or the like.

As used herein, the term "agent capable of inhibiting expression or activation of c-src" or "inhibitor for expression or activation of c-src" refers to a substance capable of inhibiting the expression or activation of c-src by directly or indirectly binding to a gene encoding c-src, mRNA, or protein. In the present specification, "agent capable of inhibiting expression or activation of c-src" may be interchangeably used with "inhibitor for c-src" or "suppressor for c-src" in the same meaning.

In the present invention, the agent capable of inhibiting expression or activation of c-src may be an active ingredient of a pharmaceutical composition exhibiting the effect of preventing or treating synucleinopathy by inhibiting expression or activation of c-src, but the agent is not particularly limited thereto, and in a specific example, the agent capable of inhibiting expression of c-src is selected from the group consisting of miRNA, siRNA, shRNA, antisense oligonucleotides and combinations thereof that can complementarily bind to the mRNA of the c-src gene, and the agent capable of inhibiting the activation of c-src is selected from the group consisting of antibodies, aptamers, small molecules and combinations thereof that can complementarily bind to the protein of c-src.

As used herein, the term "miRNA, siRNA, or shRNA" refers to a nucleic acid molecule that inhibits translation of the mRNA by binding to the mRNA transcribed mainly from the target gene in order to mediate RNA interference or gene silencing. siRNA or shRNA can inhibit the expression of the target gene at the translation level and thus can be used in an efficient gene knockdown method or gene therapy method, and can be used to inhibit the expression of c-src for the objects of the present invention.

In the present invention, the shRNA may be represented by the nucleotide sequence of SEQ ID NO: 1 or SEQ ID NO: 2, but is not limited thereto.

```
shRNA (c-src KD #1):
                                        (SEQ ID NO: 1)
CCGGGCUCGGCUCAUUGAAGACAAUCUCGAGAUUGUCUUCAAUGAGCCG
AGCUUUUUG shRNA (c-src KD #2):
                                        (SEQ ID NO: 2)
CCGGGACAGACCUGUCCUUCAAGAACUCGAGUUCUUGAAGGACAGGUCU
GUCUUUUUG
```

As used herein, the term "antisense oligonucleotide" refers to DNA or RNA that contains a nucleic acid sequence complementary to a specific mRNA sequence, or a derivative thereof, has an effect of inhibiting the translation of mRNA into a protein by binding to a complementary sequence in the mRNA, and can be used to inhibit the expression of c-src for the objects of the present invention.

As used herein, the term "antibody" refers to a proteinaceous molecule that can specifically bind to an antigenic site of a protein or peptide molecule. Each gene is cloned into an expression vector according to a conventional method to obtain a protein encoded by a marker gene, and such an antibody can be produced from the obtained protein through a conventional method.

In the present invention, the antibody can be interpreted as a means that is capable of inhibiting the activation of the protein by binding to the activated c-src protein of a subject suspected of developing a degenerative brain disease. As a specific example, the antibody of the present invention includes a polyclonal antibody, a monoclonal antibody, an antibody having an antigen-binding property or a fragment thereof that can specifically bind to c-src, and all immunoglobulin antibodies as well as special antibodies such as humanized antibodies. In addition, the antibody may have a complete form including two full-length light chains and two full-length heavy chains or a partial form including a functional fragment of an antibody molecule. The functional fragment of the antibody molecule refers to a fragment that has at least an antigen-binding function, and may be Fab, F(ab'), F(ab')2, Fv, and the like.

As used herein, the term "aptamer" refers to a nucleic acid molecule having binding activity to a predetermined target molecule. The aptamer may be RNA, DNA, a modified nucleic acid, or a mixture thereof, and may be in a linear or cyclic form. In general, it is known that, as the length of the nucleotide sequence constituting the aptamer decreases, chemical synthesis and mass production are easier, advantages in terms of costs are excellent, chemical modification is easier, in-vivo stability is superior, and toxicity is lower.

In the present invention, the aptamer may be interpreted as a means capable of inhibiting the activation of the protein by binding to the activated c-src protein.

As used herein, the term "small molecule" refers to an organic compound having a small molecular weight and a molecule that binds to a biopolymer such as a protein to control the functions thereof. It may be naturally derived or artificially synthesized, and may inhibit the function of a protein or interfere with a protein-protein interaction, but is not limited thereto.

For the purposes of the present invention, any small molecule may be used without limitation so long as it inhibits the activation of the activated c-src protein, and a specific example thereof is a molecule that binds to the activated c-src to inhibit the activation thereof, but is not limited thereto.

In another aspect, the present invention is directed to a pharmaceutical composition for preventing or treating synucleinopathy comprising an inhibitor for expression or activation of c-src.

As used herein, the term "synucleinopathy" refers to a neurodegenerative disease characterized by abnormal accumulation of α-syn aggregates in neurons, nerve fibers or glial cells.

In the present invention, the synucleinopathy may be Parkinson's disease (PD), dementia with Lewy bodies (DLB) or multiple system atrophy (MSA), but is not limited thereto.

As used herein, the term "neurodegenerative disease" refers to a disease caused by damage to nerve cells, and it is estimated that aging, genetic variation, stress, and problems associated with the function of removing proteins in cells will be the causes of the onset of the neurodegenerative disease, but the exact cause thereof is not known yet.

As used herein, the term "prevention" refers to any action that suppress or delays the onset of neurodegenerative diseases such as synucleinopathy by administration of the pharmaceutical composition comprising an agent capable of inhibiting the expression or activation of c-src according to the present invention as an active ingredient.

As used herein, the term "treatment" means any action that can ameliorate or beneficially alter the symptoms of a subject developing or suspected of developing a neurodegenerative disease such as synucleinopathy by administration of the pharmaceutical composition.

The therapeutic effect for synucleinopathy by the inhibitor for expression or activation of the c-src protein according to the present invention can be achieved through the function of inhibiting aggregation and/or migration of α-Synuclein (α-Syn) by the inhibitor for expression or activation of the c-src protein.

The pharmaceutical composition of the present invention may be prepared in the form of a pharmaceutical composition for treating synucleinopathy, which further comprises an appropriate carrier, excipient or diluent commonly used in the preparation of pharmaceutical compositions, and the carrier may include a non-naturally occurring carrier. Specifically, the pharmaceutical composition may be formulated according to a conventional method in the form of an oral formulation such as a powder, granule, tablet, capsule, suspension, emulsion, syrup or aerosol, an external preparation, a suppository, or a sterile injectable solution.

Specific examples of the carrier, excipient or diluent included in the pharmaceutical composition comprise lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil and the like.

In the case of formulation, the pharmaceutical composition may be prepared using a diluent or excipient such as a commonly used filler, extender, binder, wetting agent, disintegrant or surfactant.

Solid formulations for oral administration may include tablets, pills, powders, granules, capsules and the like, and may be prepared by mixing at least one excipient, for example, starch, calcium carbonate, sucrose, lactose, gelatin or the like. In addition to simple excipients, lubricants such as magnesium stearate and talc are also used.

Liquid formulations for oral administration may be suspensions, oral liquids and solutions, emulsions, syrups and the like, and may contain various excipients such as wetting agents, sweeteners, fragrances, preservatives and the like, in addition to water and liquid paraffin, which are simple diluents that are commonly used.

Formulations for parenteral administration may include sterilized aqueous solutions, non-aqueous solutions, suspensions, emulsions, freeze-dried preparations and suppositories. Examples of non-aqueous solutions and suspensions include propylene glycol, polyethylene glycol, vegetable oil such as olive oil, injectable esters such as ethyl oleate, and the like.

Examples of the suppository base include Witepsol, macrogol, Tween 61, cacao butter, laurin butter, glycerogelatin and the like.

The content of the agent for inhibiting expression or activation of c-src that can be contained in the pharmaceutical composition according to the present invention is not particularly limited, and is about 0.0001 to 50% by weight, more specifically, 0.01 to 20% by weight, based on the total weight of the final composition.

The pharmaceutical composition of the present invention may be administered in a pharmaceutically effective amount, and the term "pharmaceutically effective amount" refers to an amount which is sufficient for treating a disease at a reasonable benefit/risk ratio applicable to all medical treatments, and the effective dosage level may vary depending on a variety of factors including severity of the disease, activity of the drug, the age, body weight, state of health and gender of the patient, sensitivity of the patient to the drug, administration time, administration route and excretion rate of the composition according to the present invention, treatment period, drugs mixed with the used composition or used concurrently therewith, and other factors well-known in the pharmaceutical field. The pharmaceutical composition of the present invention may be administered alone or in combination with other therapeutic agents. Taking into consideration these factors, it is important to administer the minimum amount sufficient to achieve maximum efficacy without side effects.

In addition, the dose (administered amount) of the pharmaceutical composition according to the present invention may be determined by those skilled in the art in consideration of the purpose of use, severity of the disease, patient's age, weight, gender, history, or types of substance used as an active ingredient. For example, the pharmaceutical composition may be administered to an adult in a dose of about 0.1 ng/kg to about 100 mg/kg, specifically about 1 ng/kg to about 10 mg/kg. The frequency of administration of the composition of the present invention is not particularly limited, and the composition may be administered once a day or divided into several doses throughout the day. Thus, the dose is not intended to limit the scope of the invention in any aspect.

In another aspect, the present invention is directed to a method of preventing or treating synucleinopathy comprising administering the inhibitor for expression or activation of c-src to a subject.

As used herein, the term "subject" is intended to include, without limitation, mammals including mice, livestock, humans, and the like, farmed fish, and the like, that are likely to develop or have developed synucleinopathy.

The pharmaceutical composition for preventing or treating synucleinopathy of the present invention may be administered through any general route that enables the composition to reach the target tissue. The pharmaceutical composition of the present invention is not particularly limited with regard thereto, and may be administrated through a route such as intraperitoneal administration, intravenous administration, intramuscular administration, subcutaneous administration, intradermal administration, oral administration, intranasal administration, intrapulmonary administration, and rectal administration. Since the agent capable of inhibiting the expression or activation of c-src may be denatured by gastric acid upon oral administration, an oral composition may be coated with an active drug or formulated so as to protect the same from degradation in the stomach. In addition, the composition may be administered using any device capable of delivering the active substance to target cells.

In another aspect, the present invention is directed to the use of the inhibitor for expression or activation of c-src for the treatment of synucleinopathy.

In another aspect, the present invention is directed to the use of the inhibitor for expression or activation of c-src for the preparation of a therapeutic agent for synucleinopathy.

In another aspect, the present invention is directed to a method of screening a therapeutic agent for synucleinopathy, the method comprising (i) treating a nerve-tissue-derived cell with a candidate substance for a therapeutic agent for synucleinopathy, (ii) measuring the level of expression or activation of c-src protein in the cell, and (iii) selecting a candidate substance that has a reduced expression or activation level of the c-src protein compared to a control group not treated with the candidate substance.

In the step (ii) of measuring the level of expression or activation of the c-src protein, as described above, a conventional method for measuring the expression level used in the art may be used without limitation, and the measurement method may be selected from the group consisting of immunofluorescence, enzyme immunoassay (ELISA), Western blot, flow cytometry (FACS), immunohistochemistry, immunoprecipitation, radioimmunoassay (RIA), and RT-PCR.

In addition, the nerve-tissue-derived cell treated with the candidate substance for the therapeutic agent for synucleinopathy are not particularly limited, and may be, for example, a neuron or glial cell, and other examples thereof include glial cells such as microglia, astrocytes, oligodendrocytes, ependymal cells, Schwann cells and satellite cells, and preferably, the nerve-tissue-derived cell is a cell from the dopaminergic neuronal cell line SHSY5Y.

As used herein, the term "candidate substance for a therapeutic agent for synucleinopathy" refers to a substance that is expected to be able to treat synucleinopathy, and may be any substance without limitation, so long as it is expected to ameliorate or alleviate synucleinopathy directly or indirectly. The candidate substance for a therapeutic agent for synucleinopathy includes all predictable therapeutic substances such as compounds, genes or proteins.

The screening method of the present invention may further comprise determining whether or not c-src is activated before and after administration of the candidate substance and determining the candidate substance to be a therapeutic agent for synucleinopathy when the activation of c-src after administration is inhibited compared to before administration of the candidate substance.

In another aspect, the present invention is directed to a composition for diagnosing synucleinopathy comprising a substance capable of measuring the activation level of c-src.

As used herein, the term "substance capable of measuring the activation level of c-src" refers to an agent capable of determining whether or not c-src is phosphorylated, and for the purposes of the present invention, the substance capable of measuring the activation level of c-src is a substance that can be used to evaluate the effects of aggregated α-syn on cells. The substance is not particularly limited thereto, and in a specific example may be an antibody or aptamer capable of specifically binding to activated c-src.

As used herein, the term "antibody" refers to a proteinaceous molecule that can specifically bind to an antigenic site of a protein or peptide molecule. Each gene is cloned into an expression vector according to a conventional method to obtain a protein encoded by a marker gene, and such an antibody can be produced from the obtained protein through a conventional method.

For the purposes of the present invention, the antibody may be interpreted as a means that is capable of determining whether or not c-src protein is activated by binding to the activated c-src protein of a subject suspected of developing synucleinopathy. As a specific example, the antibody of the present invention includes a polyclonal antibody, a monoclonal antibody, an antibody having an antigen-binding property or a fragment thereof that can specifically bind to c-src, and all immunoglobulin antibodies as well as special antibodies such as humanized antibodies.

In addition, the antibody may be a complete form including two full-length light chains and two full-length heavy chains, or a partial form including a functional fragment of an antibody molecule. The functional fragment of the antibody molecule is a fragment that has at least an antigen-binding function, and may be Fab, F(ab'), F(ab')2, Fv, and the like.

As used herein, the term "aptamer" refers to a nucleic acid molecule having binding activity to a predetermined target molecule. The aptamer may be RNA, DNA, a modified nucleic acid, or a mixture thereof, and may be in a linear or cyclic form. In general, it is known that, as the length of the nucleotide sequence constituting the aptamer decreases, chemical synthesis and mass production are easier, advantages in terms of costs are excellent, chemical modification is easier, in-vivo stability is superior, and toxicity is lower.

For the purposes of the present invention, the aptamer may be interpreted as a means capable of determining whether or not c-src protein is activated by binding to the activated c-src protein.

As used herein, the term "diagnosis" refers to an action of detecting the existence or characteristics of a pathological condition, and for the purposes of the present invention, an action of detecting the onset of neurodegenerative diseases such as synucleinopathy, as well as an action of detecting the course of the recurrence, metastasis, drug responsiveness, resistance and the like of the subject after treatment of neurodegenerative diseases.

As used herein, the term "subject" includes, without limitation, horses, dogs, cats, pigs, goats, rabbits, hamsters, monkeys, guinea pigs, rats, mice, lizards, snakes, sheep, cattle, fish, and birds, and means any animal (e.g., human). More broadly, the subject includes cell lines of the animal without limitation.

In another aspect, the present invention is directed to a kit for diagnosing synucleinopathy comprising the composition.

The kit for diagnosing synucleinopathy of the present invention may comprise a primer or probe for directly measuring the migration of alpha-synuclein, a marker for diagnosing synucleinopathy, to adjacent cells, or for measuring the activation of the c-src activated by alpha-synuclein, or an antibody for selectively recognizing the protein, in addition to one or more types of other constituent compositions, solutions or devices suitable for the assay method.

In addition, the kit of the present invention may comprise a substrate, an appropriate buffer solution, a secondary antibody labeled with a color-developing enzyme or a fluorescent substance, and a color-developing substrate for immunological detection of the antibody. The substrate may be a nitrocellulose membrane, a 96-well plate synthesized with polyvinyl resin, a 96-well plate synthesized with polystyrene resin, and a slide glass made of glass, the color-developing enzyme may be peroxidase, alkaline phosphatase, or the like, the fluorescent substance may be FITC, RITC or the like, and the color-developing substrate may be ABTS (2,2'-azino-bis-(3-ethylbenzothiazoline-6-sulfonic acid)) or OPD (o-phenylenediamine), TMB (tetramethyl benzidine), but is not limited thereto. In addition, in order to analyze the protein level, the method may include Western blot, ELISA (enzyme-linked immunosorbent assay), radioimmunoassay (otA), radioimmunodiffusion, Ouchterlony immunodiffusion, rocket immunoelectrophoresis, tissue immunostaining, an immunoprecipitation assay, a complement fixation assay, FACS, protein chips, and the like, but is not limited thereto.

In another aspect, the present invention is directed to a method of providing information for diagnosing synucleinopathy comprising measuring the activation level of c-src in a biological sample isolated from a subject suspected of synucleinopathy using the composition for diagnosis or the kit.

In another aspect, the present invention is directed to a method of diagnosing synucleinopathy comprising measuring the activation level of c-src in a biological sample isolated from a subject suspected of synucleinopathy using the composition or the kit.

In the present invention, when the c-src activation level is increased compared to the control group, synucleinopathy is determined to occur.

As used herein, the term "sample" is not particularly limited, as long as it exhibits a difference in the activation of c-src, a parameter for the diagnosis of synucleinopathy, and may include at least one selected from the group consisting of nerve-tissue-derived cells, whole blood, serum, blood, plasma, saliva, urine, sputum, lymph, cerebrospinal fluid, and interstitial fluid, but is not limited thereto.

In the present invention, the method for measuring the activation of c-src includes Western blot, co-immunoprecipitation assay, ELISA (enzyme-linked immunosorbent assay), real-time RT-PCR, electrophoresis, tissue immunostaining, and fluorescence-activated cell sorter (FACS), but is not limited thereto.

EXAMPLES

Hereinafter, the present invention will be described in more detail with reference to the following examples. However, it will be obvious to those skilled in the art that the following examples are provided only for illustration of the present invention, and should not be construed as limiting the scope of the present invention based on the subject matter of the present invention.

Example 1: Preparation of Recombinant α-Synuclein (α-Syn) and Aggregated α-Syn Recombinant α-synuclein (α-Syn) and aggregated α-syn were prepared (KR 10-1838802). The recombinant α-Syn was overexpressed in *E. coli* strain BL21 (DE3), and the recombinant protein was purified by a known method (Lee, S. B., et al., *Biochem. Biophys. Res. Commun.* 381, 39-43, 2009). The purified α-Syn protein was stored at −80° C. until it was used as a monomeric α-Syn. 2 mg/ml of the monomeric α-syn was incubated for 2 weeks with continuous stirring at 250 rpm at 37° C., digested by simple sonication, and then stored at −80° C. until it was used as aggregated α-syn. The aggregated α-syn prepared as described above was used in all examples of the present invention.

Example 2: Production of SHP-1 Knockdown (KD) SHSY5Y Cell Line and SHP-2 Knockdown (KD) SHSY5Y Cell Line SHP-1 expression-suppression (knockdown; KD) cell line and SHP-2 expression suppression (knockdown; KD) cell line were produced by the following method.

SHP-1/2 knockdown SHSY5Y was produced by a known method using a lentiviral construct (Sigma, St. Louis, MO) expressing shRNA of SHP-1/2 (Yoon, S., et al., *Cell Death Dis.* 5:e1494, 2014), and selected using puromycin.

Then, the amount of expression of SHP-1/2 in the prepared SHP-1/2 knockdown SHSY5Y cell line was measured through Western blot using the SHP-1/2 antibody, and the result showed that the expression of SHP-1/2 in the SHP-1/2 knockdown SHSY5Y cell line was effectively reduced.

Example 3: Preparation of Mouse Primary Neurons and Brain Lysates of A53T Heterozygous Transgenic Mice Primary neurons were isolated from the cerebral cortices of one-day-old C57BL6 mice and cultured according to the conventional literature (CHA, S. H., et al., *Mol Neurodegener.* 10:63, 2015) to obtain primary neurons of mice.

Next, the brain lysate of A53T heterozygous transgenic mice, a mouse model in which A53T, one of the mutations of α-Synuclein (α-Syn) expressed in humans, was overexpressed in genetically modified mice (B6;C3-Tg(Prnp-SNCA*A53T)83Vle/J, M83; Jackson Laboratory) of was obtained by the following method.

Brains were obtained from 9-month-old C57BL6 A53T α-syn heterozygous transgenic mice and control C57BL6 mice, as described in the previous literature (Lee, H. J., et al., *Exp. Neurobiol.* 20:181-8, 2011). Brain hemispheres were placed in 600 μl of cold RIPA (radioimmunoprecipitation assay) buffer containing a cocktail of protein inhibitor and phosphatase inhibitor and homogenized. The lysate was incubated at 4° C. for 30 minutes and was then centrifuged at 14,000 rpm at 4° C. for 30 minutes. The supernatant was obtained and Western blot was performed thereon.

Example 4: Increased Activation of c-Src by Aggregated α-Syn

The activation of c-src by agglutinated α-syn was investigated using the dopaminergic neuronal cell line (the SHSY5Y cell line), the mouse primary neurons of Example 3, and the mouse brain lysate of Example 3.

Figure 1B:
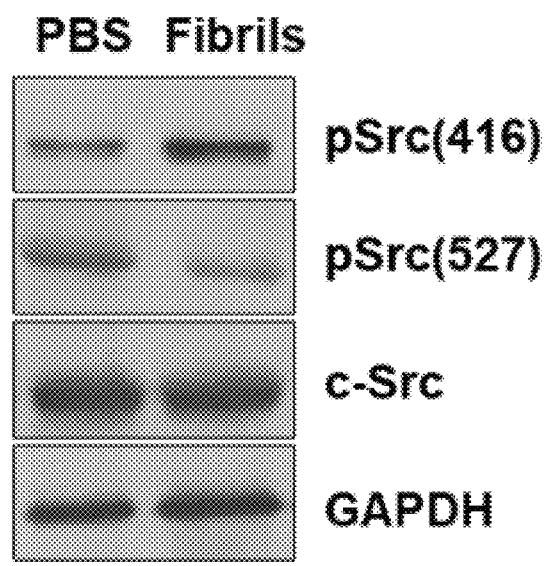
Figure 1B:
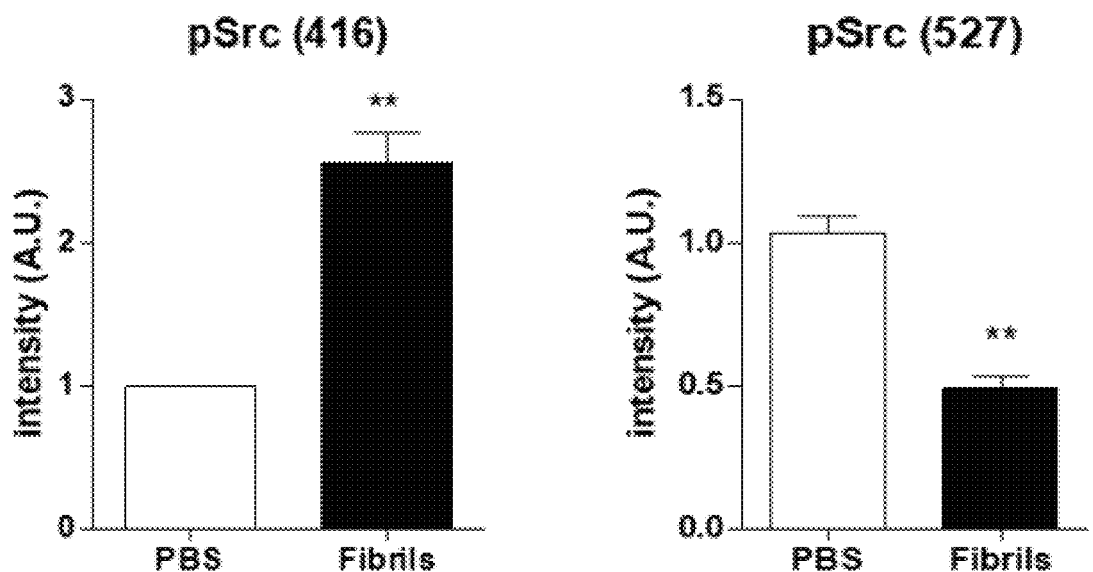
Figure 1C:
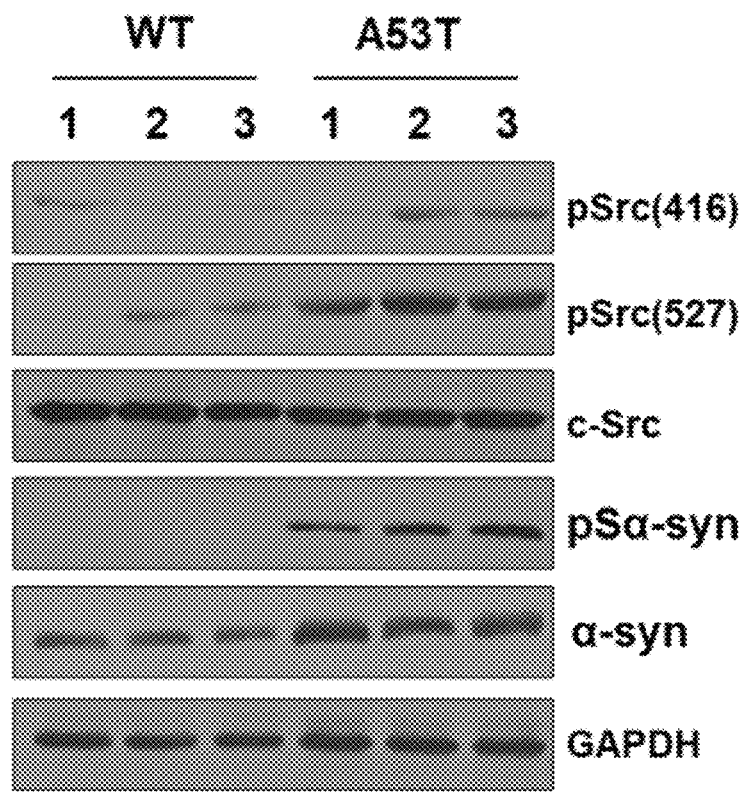
Figure 1C:
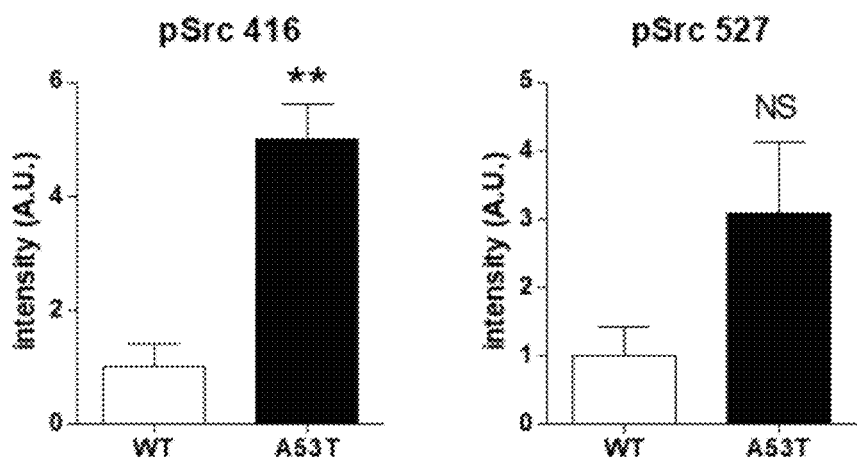

Each of the SHSY5Y cell line and the mouse primary neurons was cultured using 1 μM of aggregated α-syn for 10 minutes, lysed and subjected to Western blot (FIGS. 1A and 1B). In addition, whole brain lysates of A53T TG mice were compared with those of wild-type WT C57BL6 mice by Western blot (FIG. 1C).

Western blot was performed by lysing individual cells in cold RIPA buffer (50 mM Tris-HCl, pH 74, 1% NONIDE™ (octylphenoxypolyethoxyethanol) P-40, 0.25% sodium deoxycholate, 150 mM NaCl) containing a protein inhibitor (2 mM phenylmethylsulfonyl fluoride, 100 μg/ml leupeptin, 10 μg/ml pepstatin, 1 μg/ml aprotinin and 2 mM EDTA) and a phosphatase inhibitor cocktail (GENDEPO™, Baker, TX). After lysing the cells through sonication, the lysate was centrifuged at 14,000 rpm at 4° C. for 30 minutes and a supernatant was obtained. Protein concentration was measured using a BCA protein assay kit. Proteins were separated using SDS-PAGE, transferred to a nitrocellulose membrane, and then visualized using a chemiluminescence (ECL) system (Thermo, Waltham, MA).

As a result, it was confirmed that the activation of c-src was increased by the aggregated α-syn.

Figure 2A:
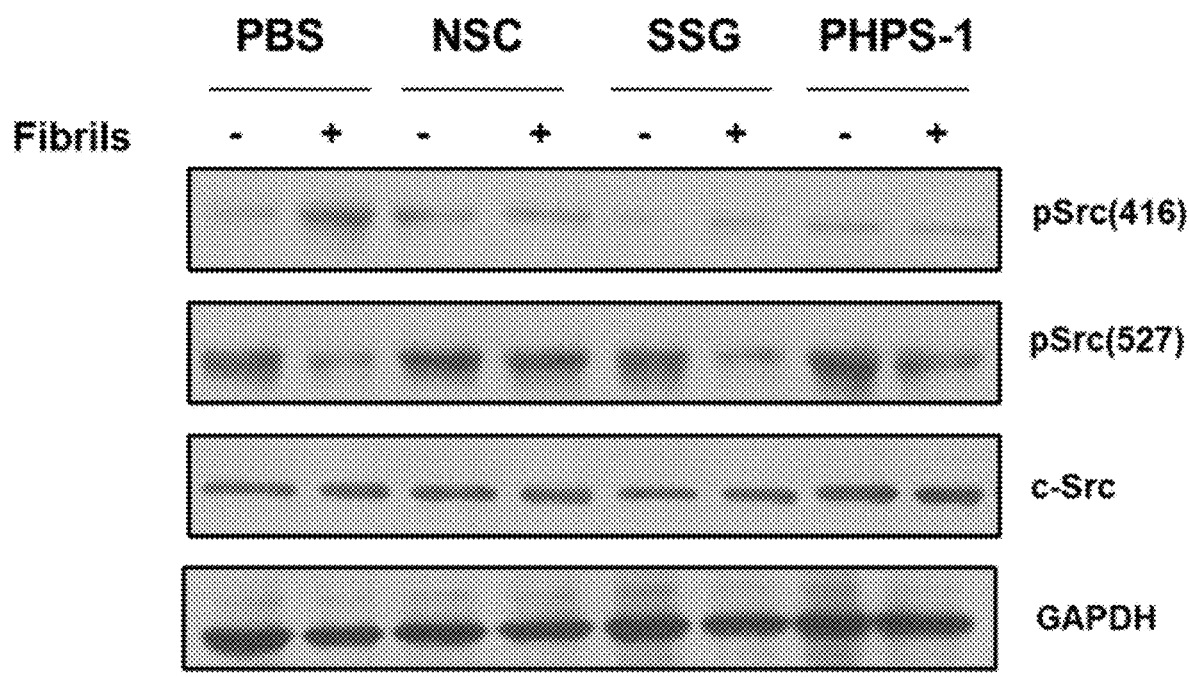
FIGS. 2A-2C show the inhibition of c-src activation by aggregated α-syn in the SHSY5Y cell line treated with inhibitors of SHP-1/2, SHP-1, and SHP-2, wherein **$P<0.01$ represents the result compared to PBS.
Figure 2B:
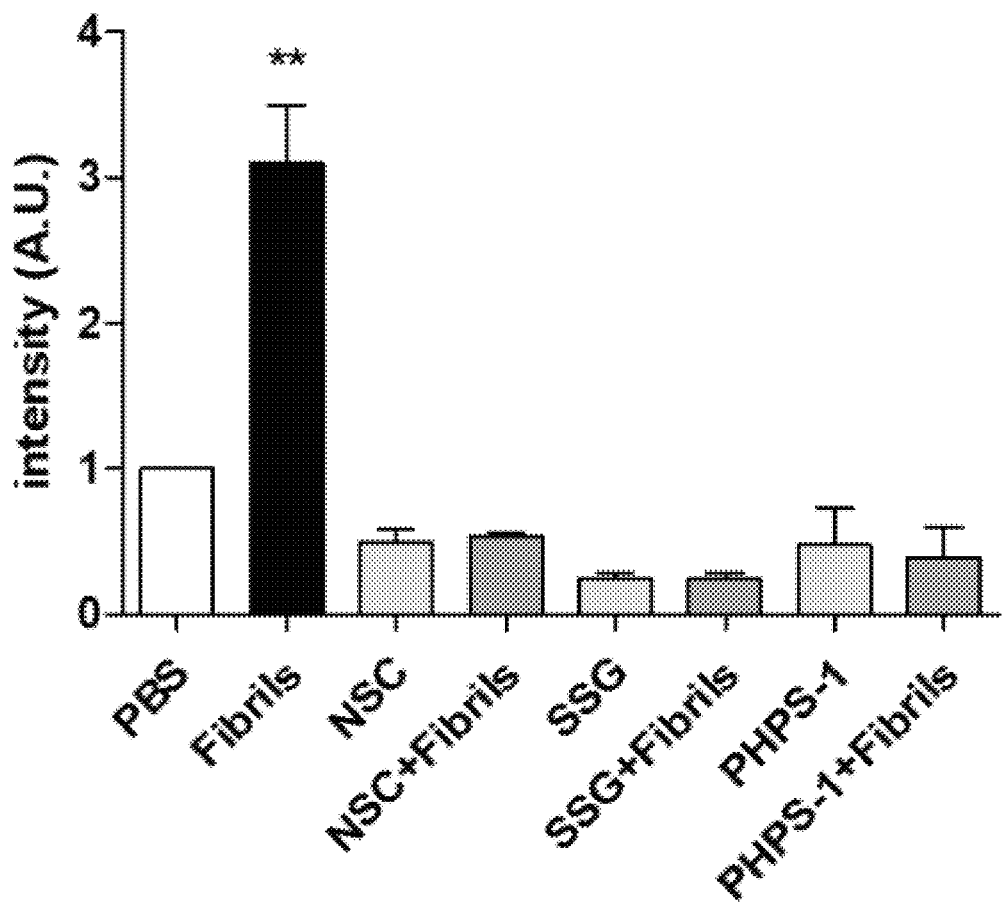
Figure 2C:
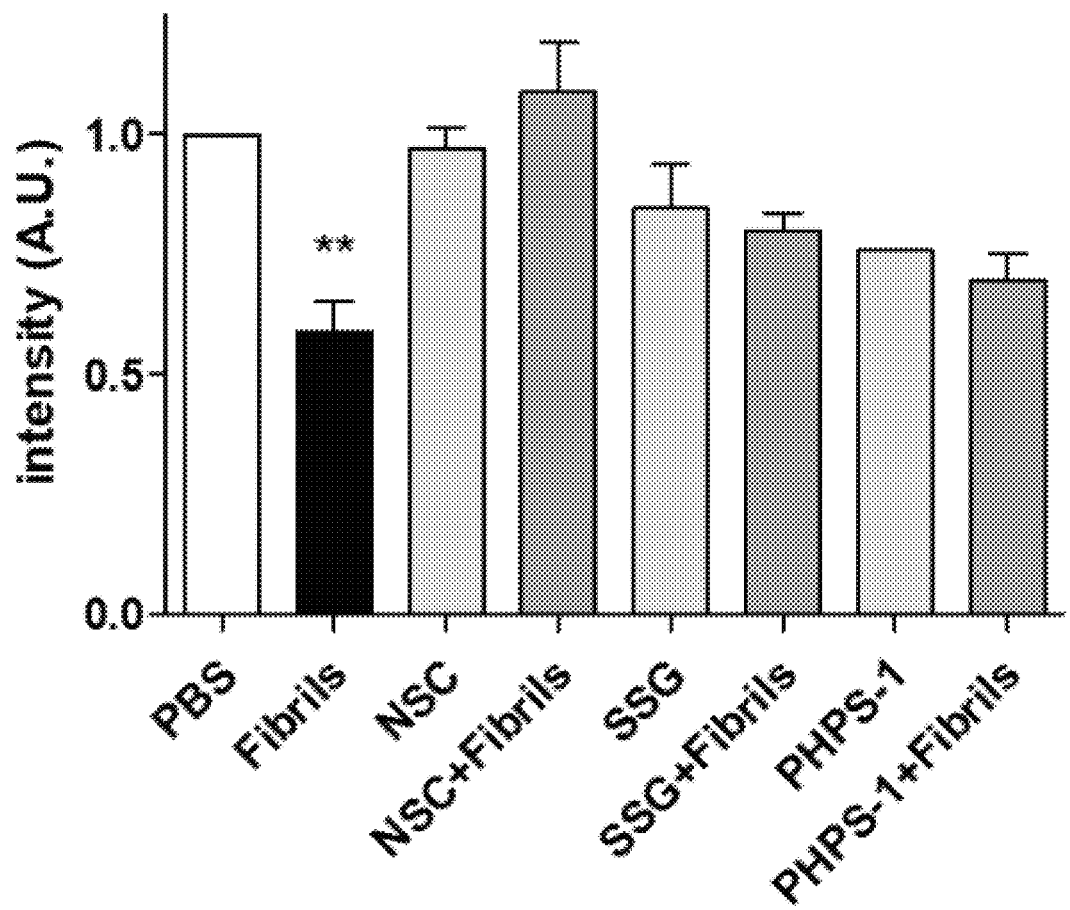

Example 5: Inhibition of c-Src Activation Mediated by Aggregated α-syn Through SHP-1 or SHP-2 Inhibition The SHSY5Y cell line was pretreated with 20 μM NSC87877 (8-hydroxy-7-[2-(6-sulfo-2-naphthalenyl)diazenyl]-5-quinolinesulfonic acid) as a SHP-1/2 inhibitor, 10 μM SSG (sodium stibogluconate) as a SHP-1 inhibitor or 1 μM PHPS-1 (4-[2-[1,5-dihydro-3-(4-nitrophenyl)-5-oxo-1-phenyl-4H-pyrazol-4-ylidene]hydrazinyl]-benzenesulfonic acid) as a SHP-2 inhibitor for 30 minutes and incubated using 1 μM of aggregated α-syn for 10 minutes, lysed and subjected to Western blot (FIGS. 2A-2C).

Figure 3A:
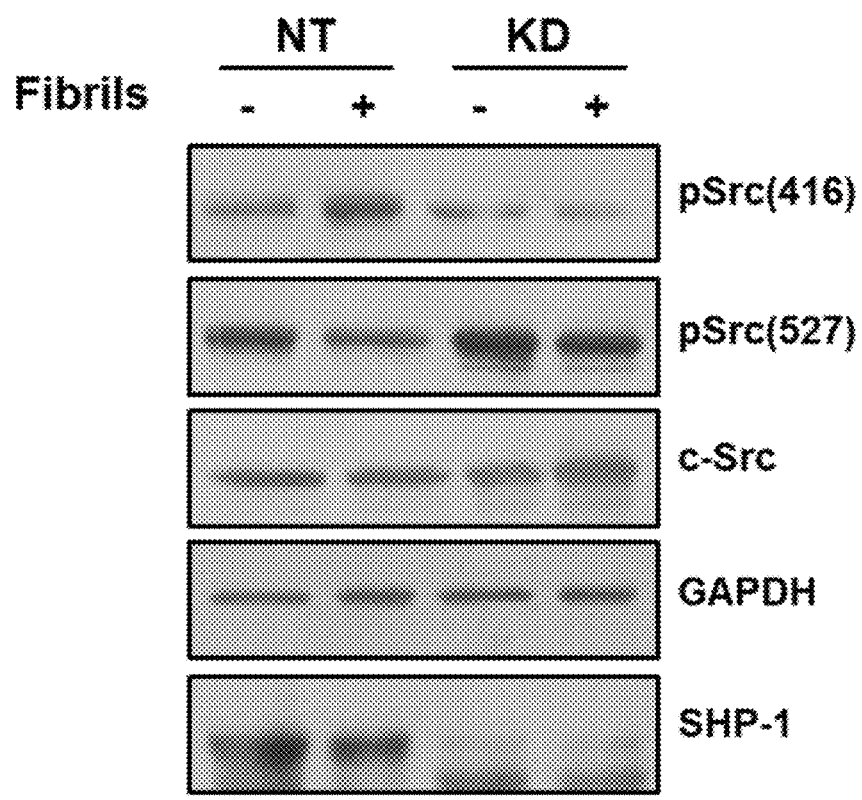
FIGS. 3A and 3B show the inhibition of c-src activation by aggregated α-syn in the SHSY5Y cell line in which the expression of SHP-1 or SHP-2 is inhibited, wherein **$P<0.01$ represents the result compared to control group (NT).
Figure 3A:
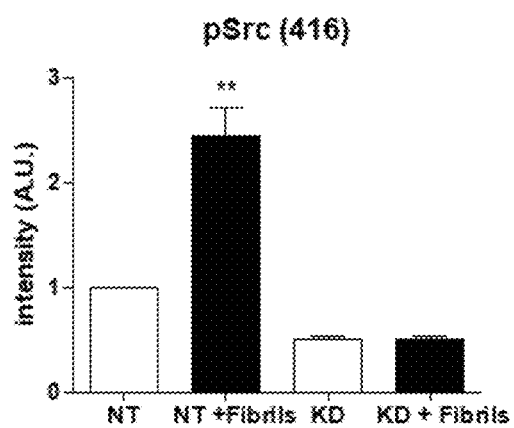
Figure 3A:
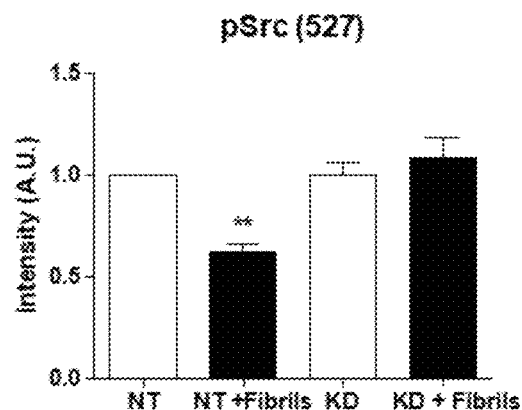
Figure 3B:
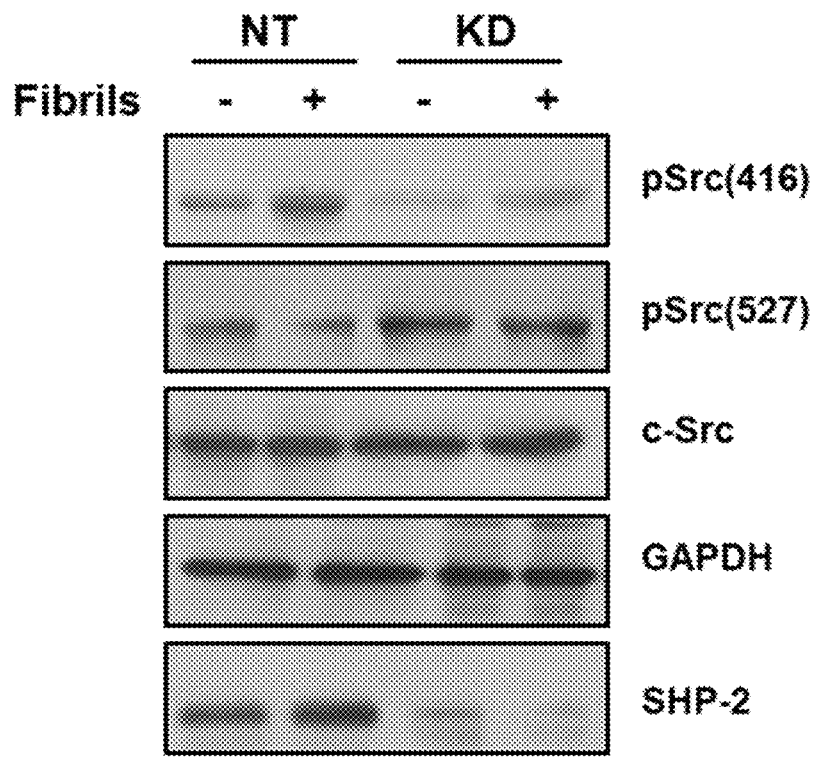
Figure 3B:
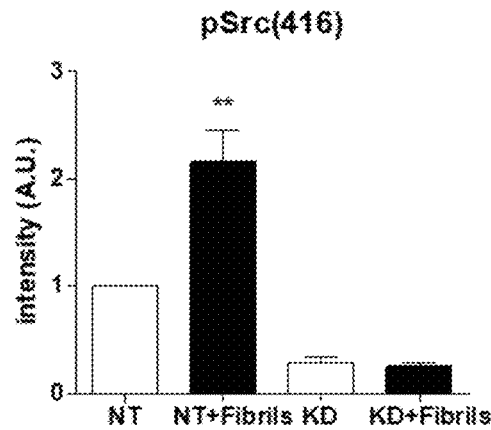
Figure 3B:
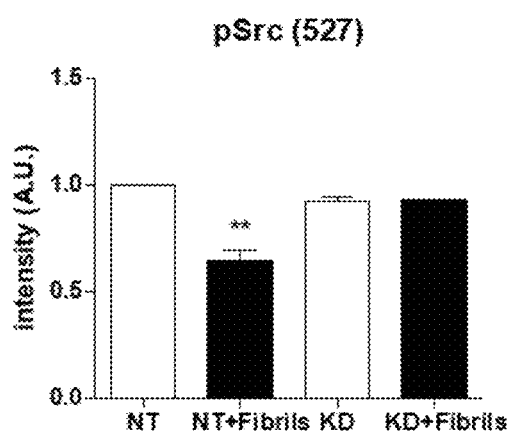

In addition, the SHP-1 knockdown SHSY5Y cell line and the SHP-2 knockdown SHSY5Y cell line produced in Example 2 were treated with 1 μM of agglutinated α-syn and cultured for 10 minutes, lysed and subjected to Western blot (FIGS. 3A-3B).

As a result, it was confirmed that when SHP-1 or SHP-2 was knocked down (suppressed), src activation mediated by the aggregated α-syn was decreased.

Example 6: Effect of c-Src on α-Syn Migration

The SHSY5Y cell overexpressing alpha-synuclein was seeded at $4 \times 10^4$ in a 12-well plate in an insert well using a two-chamber system, and the SHSY5Y cell line was seeded at $4 \times 10^4$ on the cover glass. The next day, the insert well was transferred to a 12-well cover glass, and during co-culture for 12 hours, the SHSY5Y cell line was treated with 0.1 μM saracatinib and 10 μM SKI (c-src kinase inhibitor I), which are c-src inhibitors, and then alpha-synuclein in SHSY5Y cell line on the cover glass was immunostained (α-syn: red, nucleus: blue) and observed using a confocal microscope to confirm that alpha-synuclein was migrated from SHSY5Y overexpressing alpha-synuclein to SHSY5Y not overexpressing alpha-synuclein.

Figure 4:
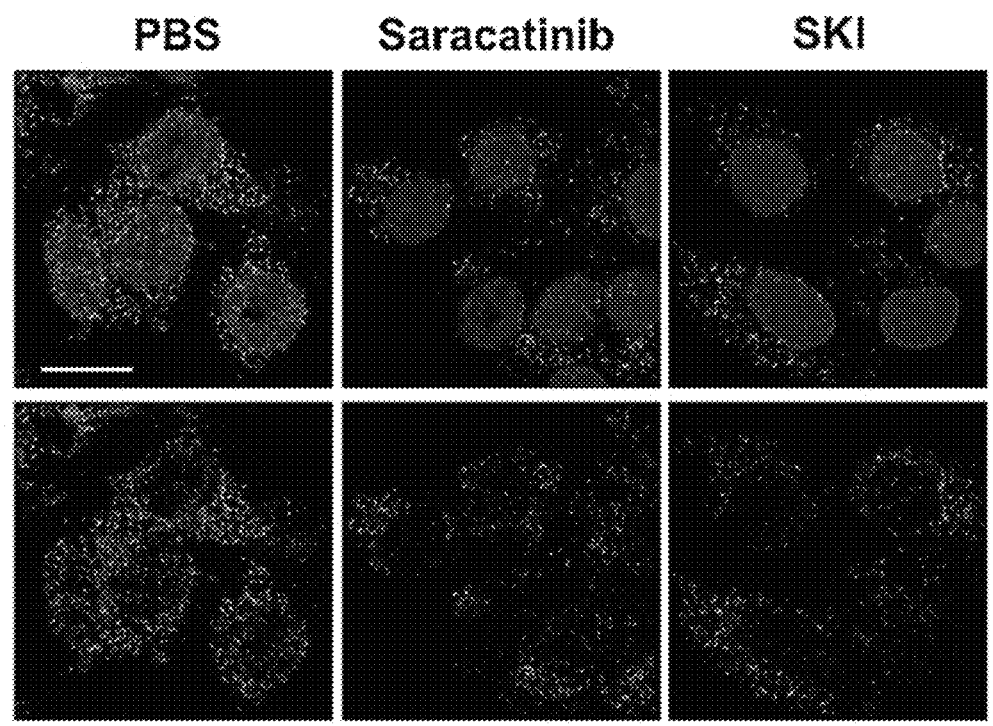
FIG. 4 shows that c-src acts on the intercellular migration of α-syn and that the migration of α-syn is reduced by treating the SHSY5Y cell line with, as a c-src inhibitor, saracatinib or SKI (Src kinase inhibitor), wherein the scale bar represents 20 μm, and **$P<0.01$ represents the result compared to PBS.
Figure 4:
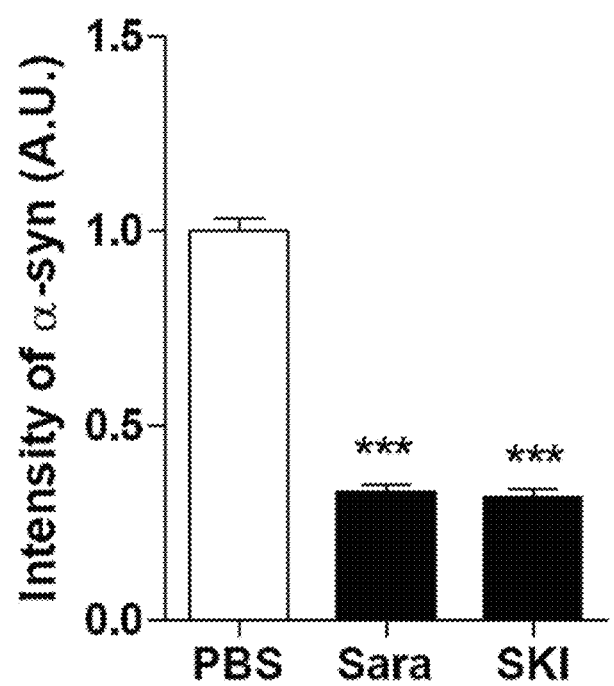

The result showed that the migration of α-syn was observed in the PBS control group, but that migration of α-syn was reduced by treatment with saracatinib and SKI (FIG. 4).

Next, c-src knockdown SHSY5Y cell lines (KD #1 and KD #2), constructed using shRNAs of SEQ ID NOS: 1 and (using lentivirus), and dopaminergic neuronal cell line SHSY5Y overexpressing α-syn were co-cultured for 12 hours using a two-chamber system. The co-culture will be described in brief. SHSY5Y cells were seeded at a concentration of $4 \times 10^4$ cells/well on a 12-well cover glass. After incubation for one day, the transwell, in which the α-syn overexpressed SHSY5Y cells were seeded, was transferred to the 12-well cover glass, on which the src knockdown SHSY5Y cells were seeded, followed by co-culture for 12 hours, immunostaining (α-syn: red, nucleus: blue), and observation with a confocal microscope.

Figure 5:
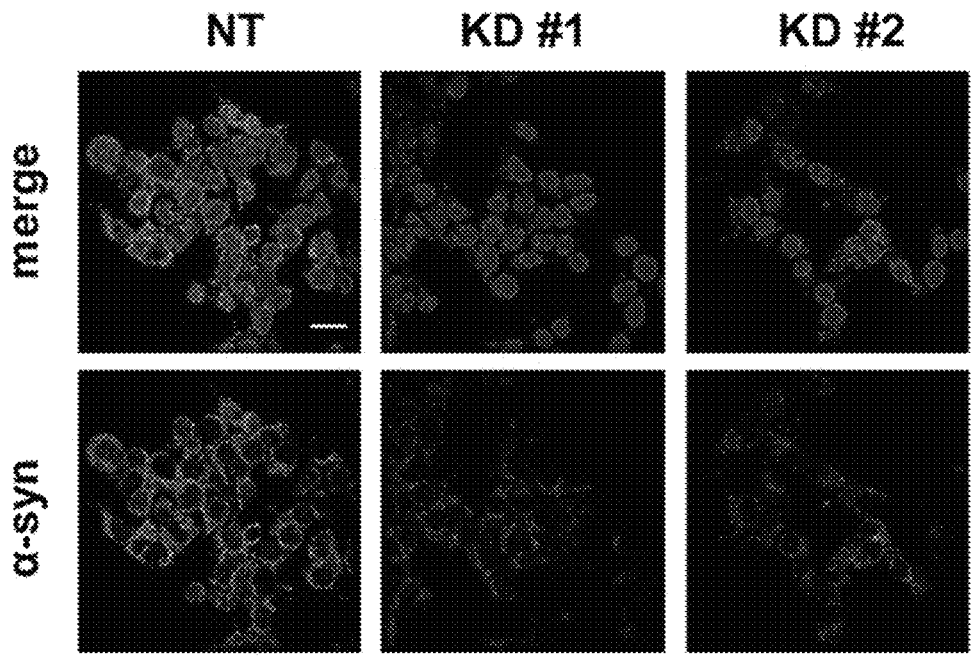
FIG. 5 shows that c-src acts on intercellular migration of α-syn and the result of microscopic observation on migration of SHSY5Y cells with inhibited c-src expression when SHSY5Y cells and SHSY5Y cells with inhibited expression of c-src are disposed on the bottom and SHSY5Y cells overexpressing α-syn are disposed on top, wherein the scale bar represents 20 μm, and **$P<0.01$ represents the result compared to control group (NT).
Figure 5:
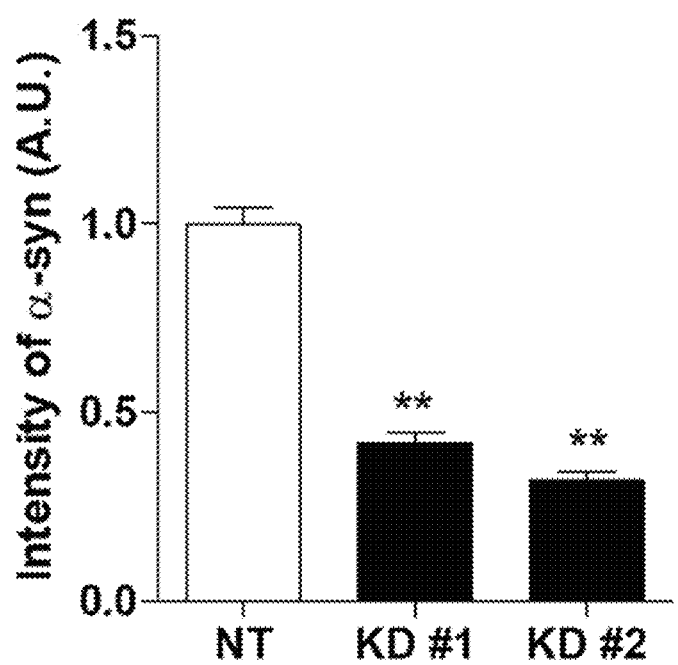

The result of observation of the migration of α-syn in the normal control group (NT; non-targeting) SHSY5Y cell line and the c-src knockdown SHSY5Y group (SHSY5Y with suppressed c-src expression) showed that the migration of α-syn was reduced by suppression of c-src expression (FIG. 5).

Example 7: Influence of c-Src on Denaturation of α-Syn Monomer to α-Syn Aggregate There is the possibility that the denaturation process in which the monomeric α-syn is converted into aggregated α-syn may be the main cause of Parkinson's disease. Therefore, the monomeric A53T α-syn was overexpressed in the SHSY5Y cell line, and whether or not c-src was involved in the process in which the overexpressed monomeric A53T α-syn is converted into aggregated A53T α-syn was determined.

Each of a SHSY5Y cell line overexpressing A53T α-syn labeled with eGFP (enhanced green fluorescent protein) and a SHSY5Y cell line overexpressing A53T α-syn labeled with mcherry (a red fluorescent protein) was produced using lentivirus in the same manner as in Example 2. Then, the SHSY5Y cell line overexpressing A53T α-syn labeled with eGFP and the SHSY5Y cell line overexpressing A53T α-syn labeled with mcherry were mixed and co-cultured. On the 5th day of co-culture, the merged distribution of eGFP and mcherry in the cells of A53T α-syn labeled with eGFP was observed with a confocal microscope, and the merged distribution of eGFP and mcherry in the cells of A53T α-syn labeled with mcherry was also observed.

Figure 6:
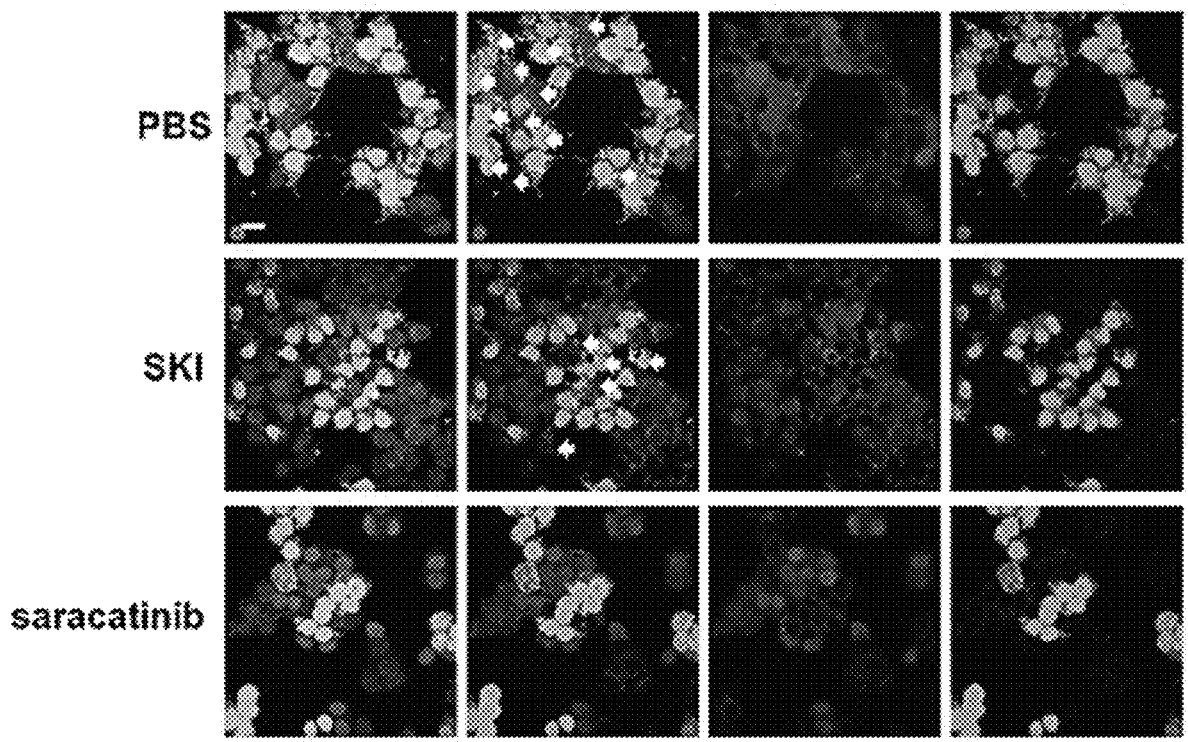
FIG. 6 is a graph showing the result of a determination as to whether or not c-src affects the process of converting the overexpressed monomeric A53T α-syn to aggregated A53T α-syn when treating the SHSY5Y cell line overexpressing the monomeric A53T α-syn with saracatinib or SKI, wherein the scale bar represents 20 μm, and **$P<0.01$ shows the result compared to PBS.
Figure 6:
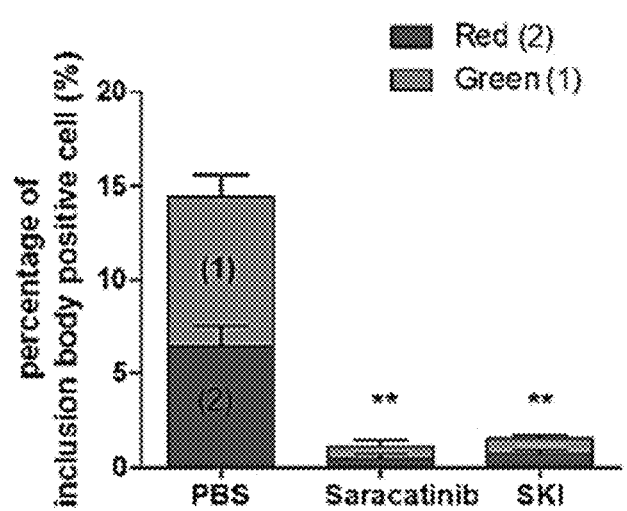
Figure 7:
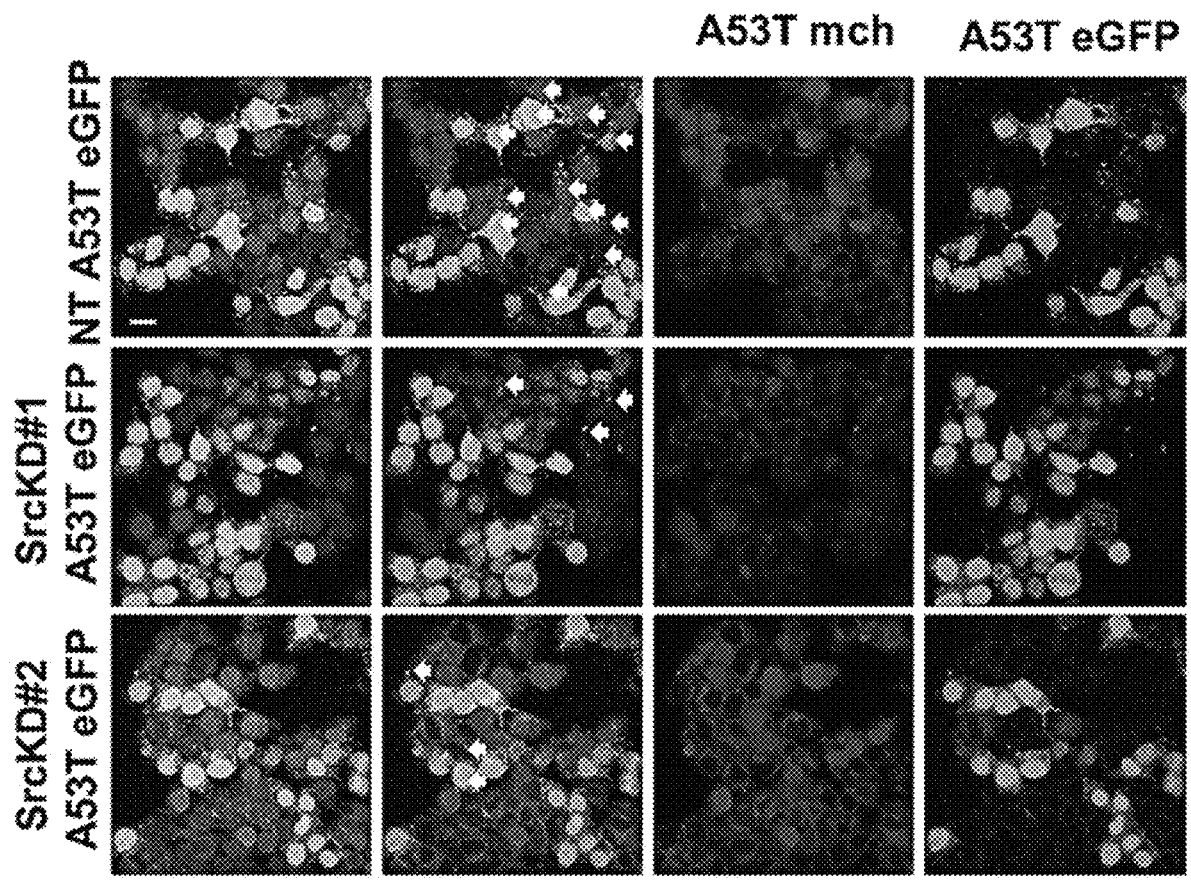
FIG. 7 is a graph for comparing the SHSY5Y cell line overexpressing the monomeric A53T α-syn with inhibited expression of c-src, with a control group, wherein the scale bar represents 20 μm, and **$P<0.01$ shows the result compared to comparative group (NT).
Figure 7:
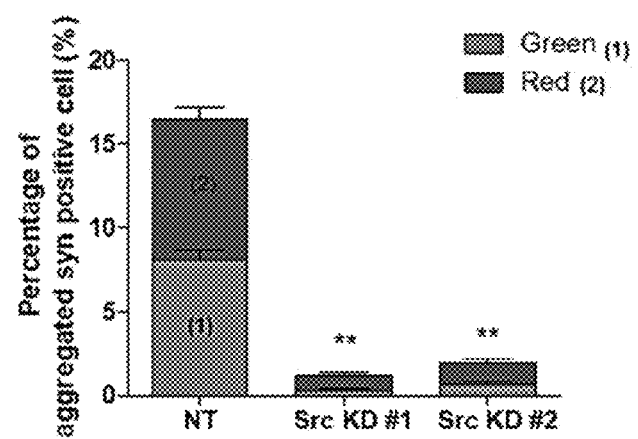

FIG. 6 shows the result of treatment of co-cultured cells of the produced SHSYSY cell line with SKI and saracatinib as c-src inhibitors. In addition, FIG. 7 show the result of observation after co-culture of A53T α-syn eGFP and A53T α-syn mcherry, which inhibited c-src expression using shRNA of SEQ ID NOS: 1 and 2.

Figure 8A:
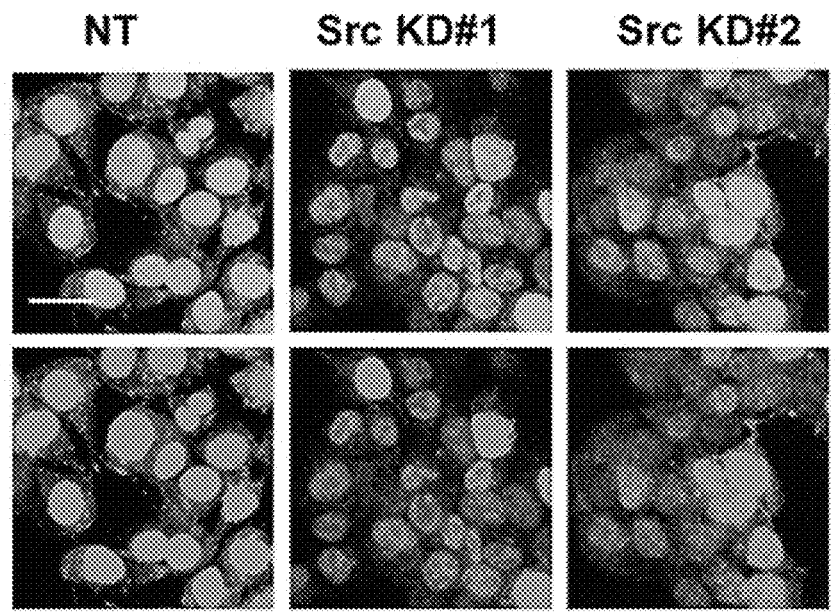
FIGS. 8A and 8B show the result of a determination as to whether or not expression and activation of c-src affect the formation of α-syn aggregates, and shows that the amount of aggregated α-syn is decreased when A53T eGFP is overexpressed, (FIG. 8A) in the case where the expression of src is inhibited and (FIG. 8B) in the case where the activation of src is inhibited, wherein the scale bar represents 20 μm.

A53T eGFP was overexpressed in Src KD SHSYSY (using the shRNA of SEQ ID NOS: 1 and 2), and cells exhibiting the eGFP signal were selected by FACS (fluorescence-activated cell sorting), cultured, treated with 50 μM of retinoid acid, differentiated for 5 days, and then imaged with a confocal microscope. The result showed that the amount of α-syn aggregated in the cells in which the expression of src was suppressed was decreased (FIG. 8A).

Figure 8B:
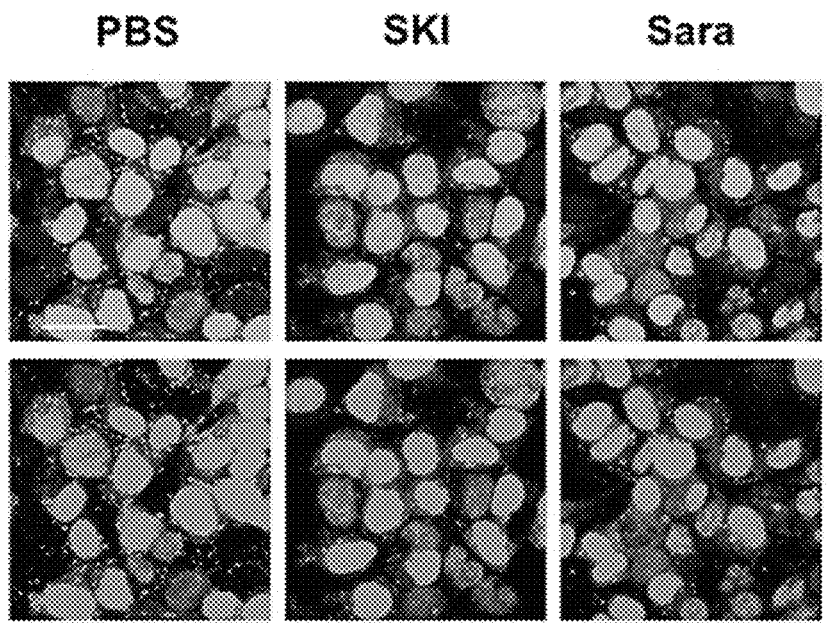

In addition, SHSY5Y overexpressing A53T eGFP was each treated with 10 μM of c-src kinase inhibitor I (SKI) and 0.5 μM of saracatinib and differentiated with 50 μM of RA (retioid acid), and the aggregated α-syn was observed with a confocal microscope. The result showed that the amount of aggregated α-syn was decreased when the activation of src was suppressed (FIG. 8B).

Figure 9:
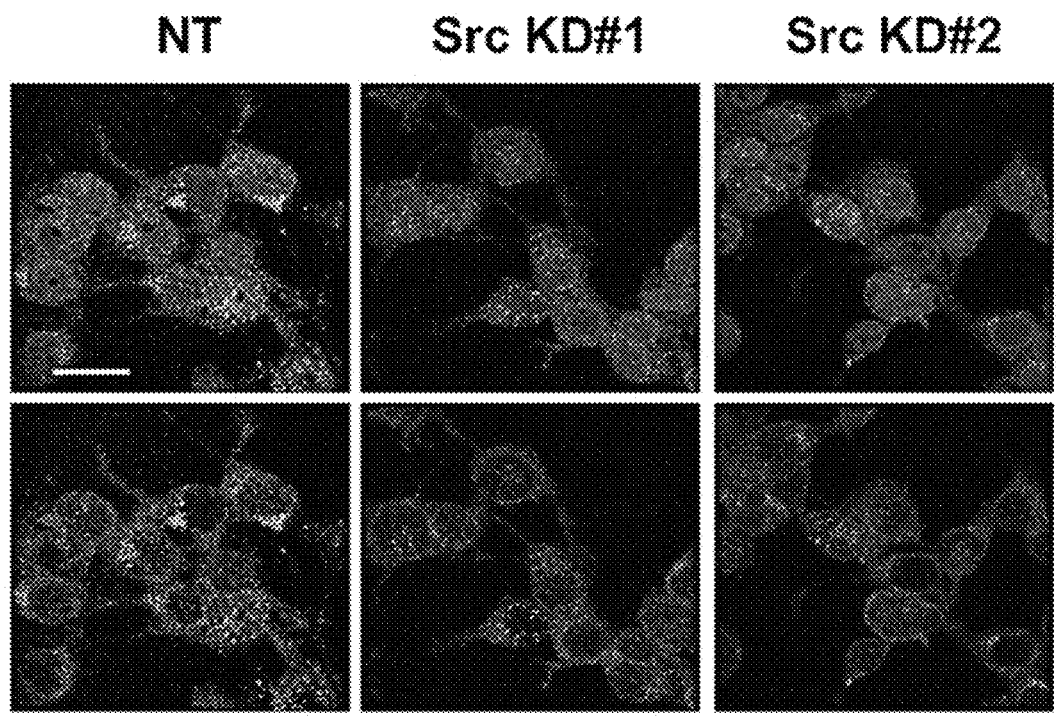
FIG. 9 is a graph for comparing the extracellular secretion of A53T α-syn in the SHSY5Y cell line overexpressing the monomeric A53T α-syn with inhibited expression of c-src, with the control group, wherein the scale bar represents 20 μm, and **$P<0.01$ show the result compared to comparative group (NT).
Figure 9:
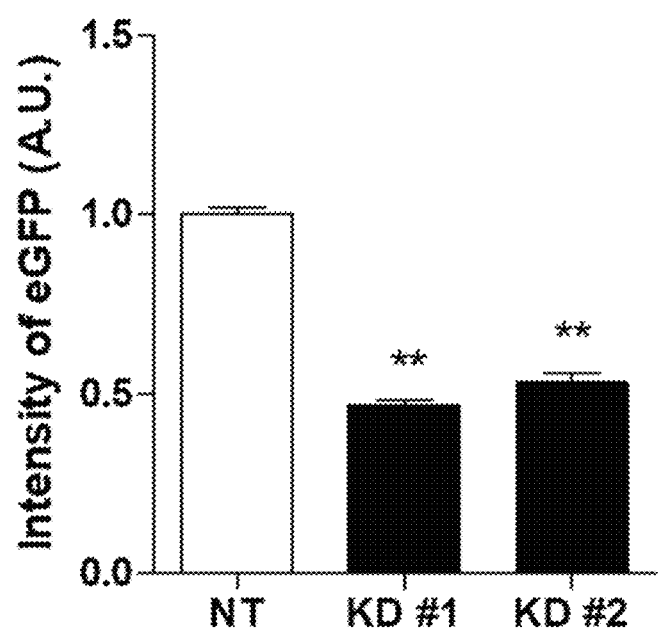

Finally, compared to the normal control group (NT; non-targeting), the SHSY5Y cell line in which c-src expression was suppressed exhibited reduced migration of A53T α-syn eGFP outside the cell (FIG. 9).

Example 8: Observation of α-Syn Migration in Transgenic Mice of α-Syn Mutant A53T It was found that the migration of α-syn in mutant mice was caused by the aggregated α-syn.

As model mice, 8- to 12-week-old transgenic mice overexpressing A53T, one of the mutations of α-synuclein (α-Syn) expressed in humans (B6;C3-Tg(Prnp-SNCA*A53T)83Vle/J, M83; Jackson Laboratory), were anesthetized by administering AVERTIN® (tribromoethanol) at a dose of 200 μl per 20 g of body weight thereto and then fixed to a stereotaxic surgical instrument, and the aggregated α-syn was injected at a dose of 10 μg into the striatum of the mice using a Hamilton syringe at coordinates of 1.0 mm in front, 1.8 mm to the right and 3.0 mm deep based on Bregma of the mouse (FIGS. 10A-10D).

Then, after 3 days of nursing, saracatinib was administered orally at a concentration of 10 mg/kg once daily over a total of 4 weeks. Then, the mice were anesthetized by administering urethane in a dose of 200 μl per 20 g of body weight, the chest was incised, perfusate was allowed to flow through the left ventricle of the heart for 3 minutes to cut the right atrium, the blood was removed, and the tissues of the mice were fixed by flowing 4% formaldehyde for 3 minutes. Then, the brain was extracted, immersed in 4% formaldehyde fixative for one day, and then dehydrated until it settled to the bottom of 30% sugar water. Then, when the brain was observed to settle to the bottom, the brain was loaded on a fixing plate, and the compound was frozen at −20° C. with OCT Compound and then frozen again at −80° C. for 30 minutes to produce brain sections with a thickness of 35 μm. The brain sections were stored in tissue storage liquid.

When the brain sections were used for tissue immunostaining, the brain sections were taken out and washed three times with PBS for 10 minutes (hereinafter, after reacting with each specific solution, washing three times), and then peroxidase in the tissue was removed with 3% hydrogen peroxide solution for 5 minutes. After washing and blocking with a blocking solution (1% BSA, 0.2% Triton X-100) for 1 hour, pSyn #64 primary antibody (WAKO™ #01525191) targeting the aggregated α-syn was reacted at a concentration of 1:5,000 and the secondary antibody was reacted at a concentration of 1:5,000, the antibodies attached to the tissue were reacted with the ABC complex, and then a color reaction was induced with 3'3-diaminobenzidine. Then, the tissue was attached to a microglass, dried and hydrated with 100%, 70%, and 20% ethanol, and then the nuclei were stained with hematoxylin and dehydrated sequentially in 70, 80, 90 and 100% ethanol. Then, the tissue was reacted with xylene for about a day, was placed on the glass, a mount solution was placed thereon, and the result was covered with a cover glass, and analyzed at a magnification of 400× using a dissecting microscope.

Figure 10A:
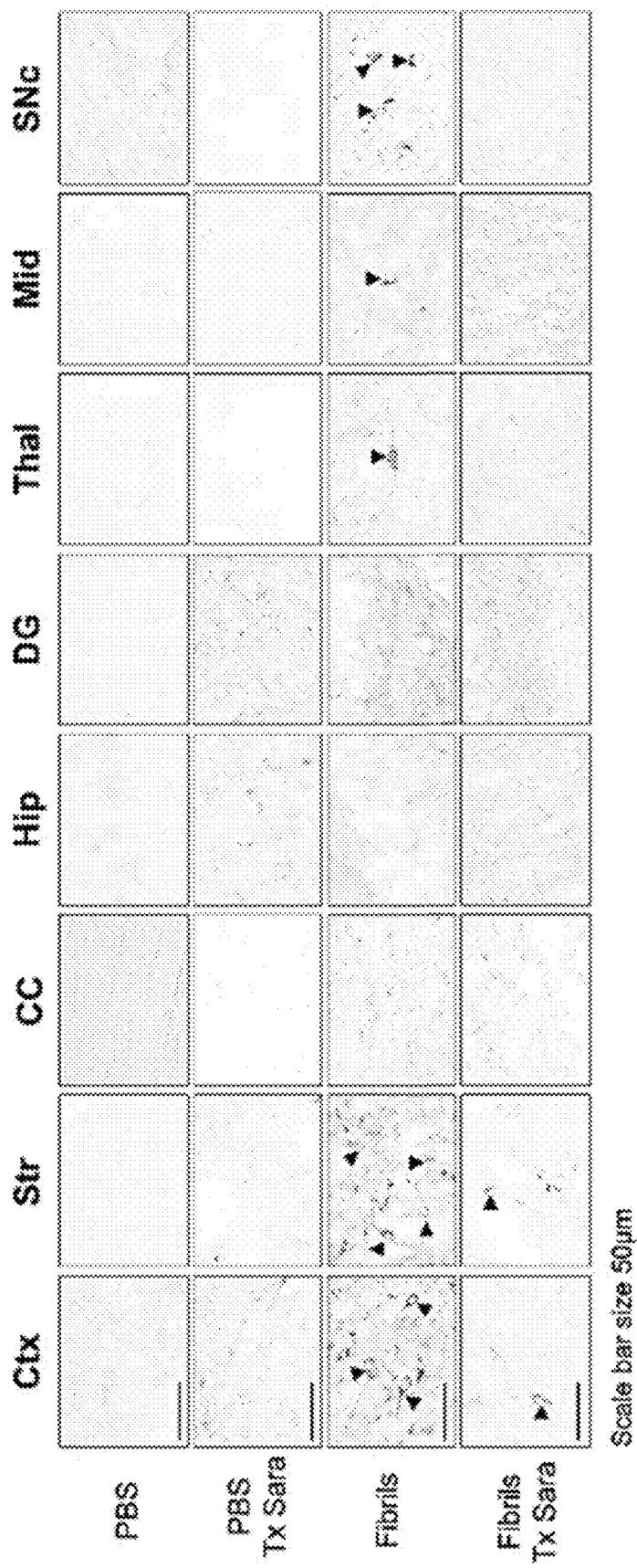
FIG. 10A shows that a Lewy body in brain tissue is observed by DAB staining after administration of saracatinib to a mutant mouse, induced by injecting aggregated α-syn into the brain of an A53T α-syn mutant mouse (scale bar is 50 μm)
Figure 10B:
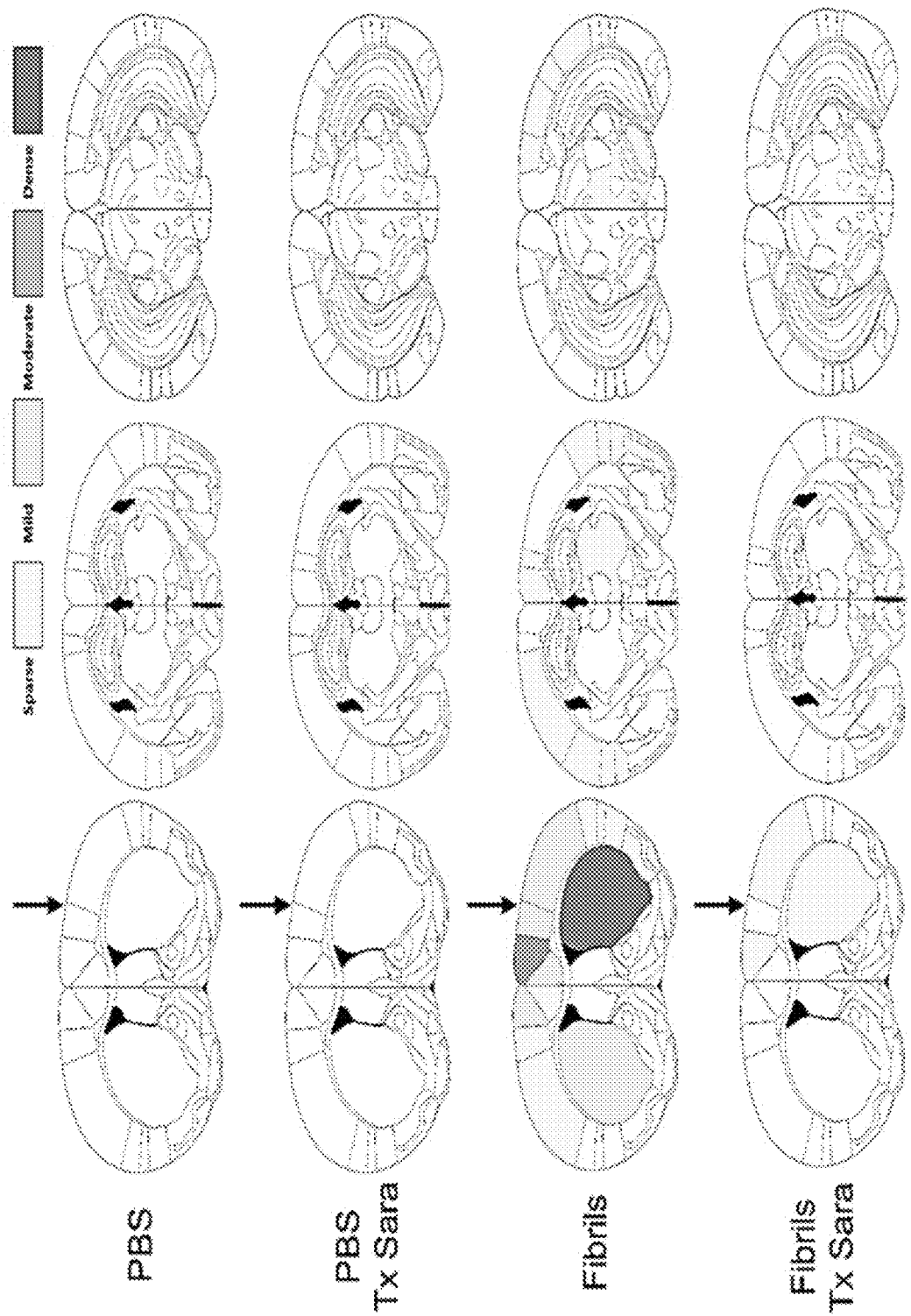
FIG. 10B is an image showing the distribution level of the Lewy body in color.
Figure 10C:
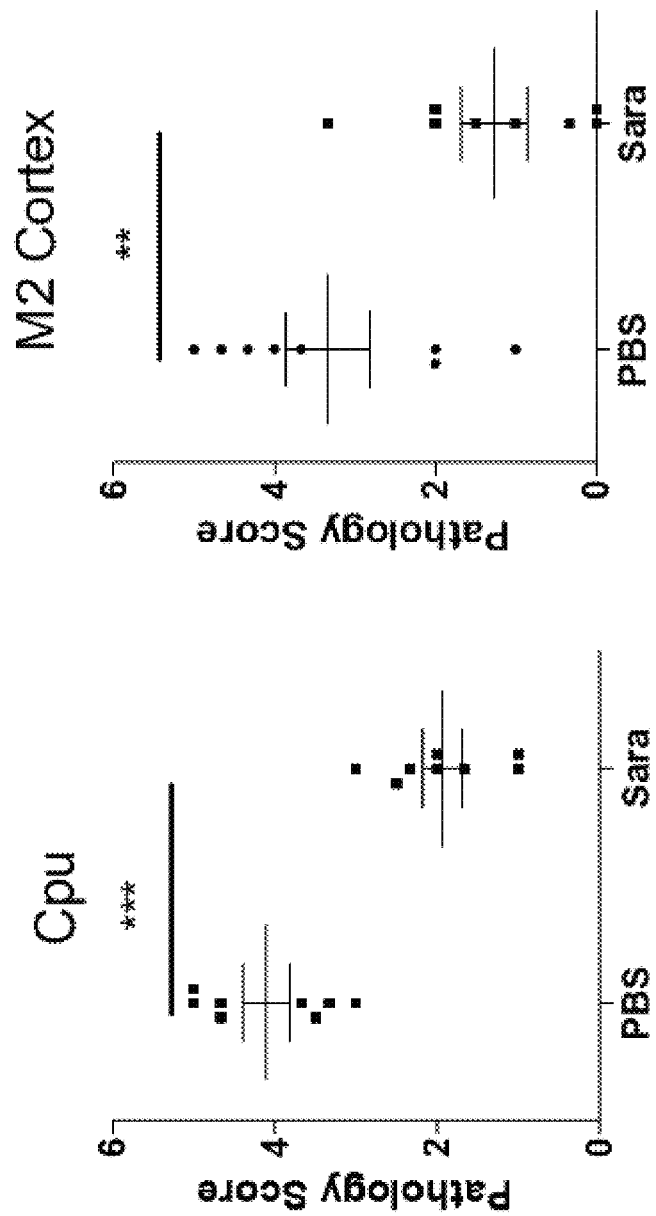
FIGS. 10C and 10D are graphs obtained by dividing the Lewy body into respective regions of brain tissue and quantifying the same, wherein **P<0.01 shows the result compared to comparative group (PBS).
Figure 10D:
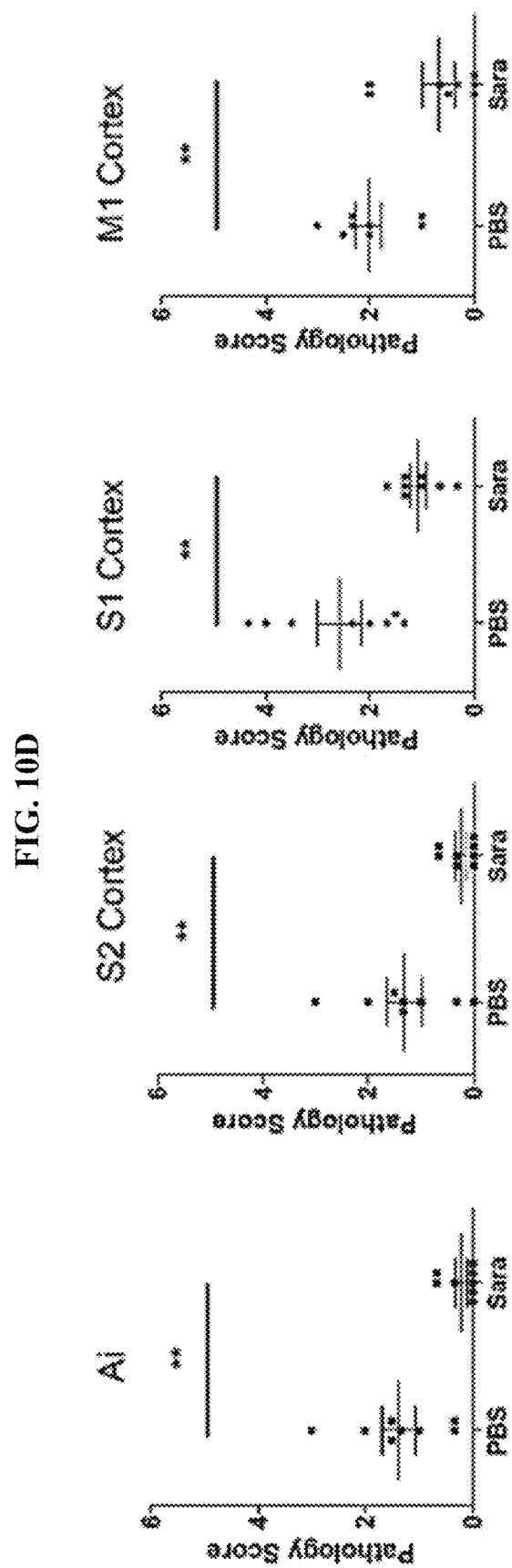

The brain tissues of the group in which each of 10 μg of the aggregated α-syn and PBS were administered to the transgenic mice of the α-Syn mutant A53T for 4 weeks and the group in which the aggregated α-syn was administered and saracatinib was injected daily at 10 mg/kg were obtained by the method described above, and then the Lewy bodies were stained by a DAB staining method, and the migration of α-syn at each site was observed. The results are shown in FIG. 10A. FIGS. 10B-10D are an image and graph showing the degree of α-syn migration for each region of brain tissue.

Example 9: Determination of Reduction of α-Syn Migration by Inhibition of c-Src Expression or Activation The cortex was isolated from rat TP18 (fetuses on the 18th day of pregnancy), and primary neurons were cultured in neural basal media for 14 days. On the 14th day, the expression of src was inhibited using lentivirus (using NT and src KD #1 virus).

In order to confirm the effect of c-src expression inhibition on α-syn migration, a dual chamber assay was performed after differentiating SHSY5Y overexpressing A53T eGFP in 50 μM RA (retinoid acid) for days. In order to confirm the effect of c-src activation inhibition on α-syn migration, primary neurons were treated with 10 μM SKI and 0.5 μM saracatinib on day 14 and a dual chamber assay was performed.

Figure 11A:
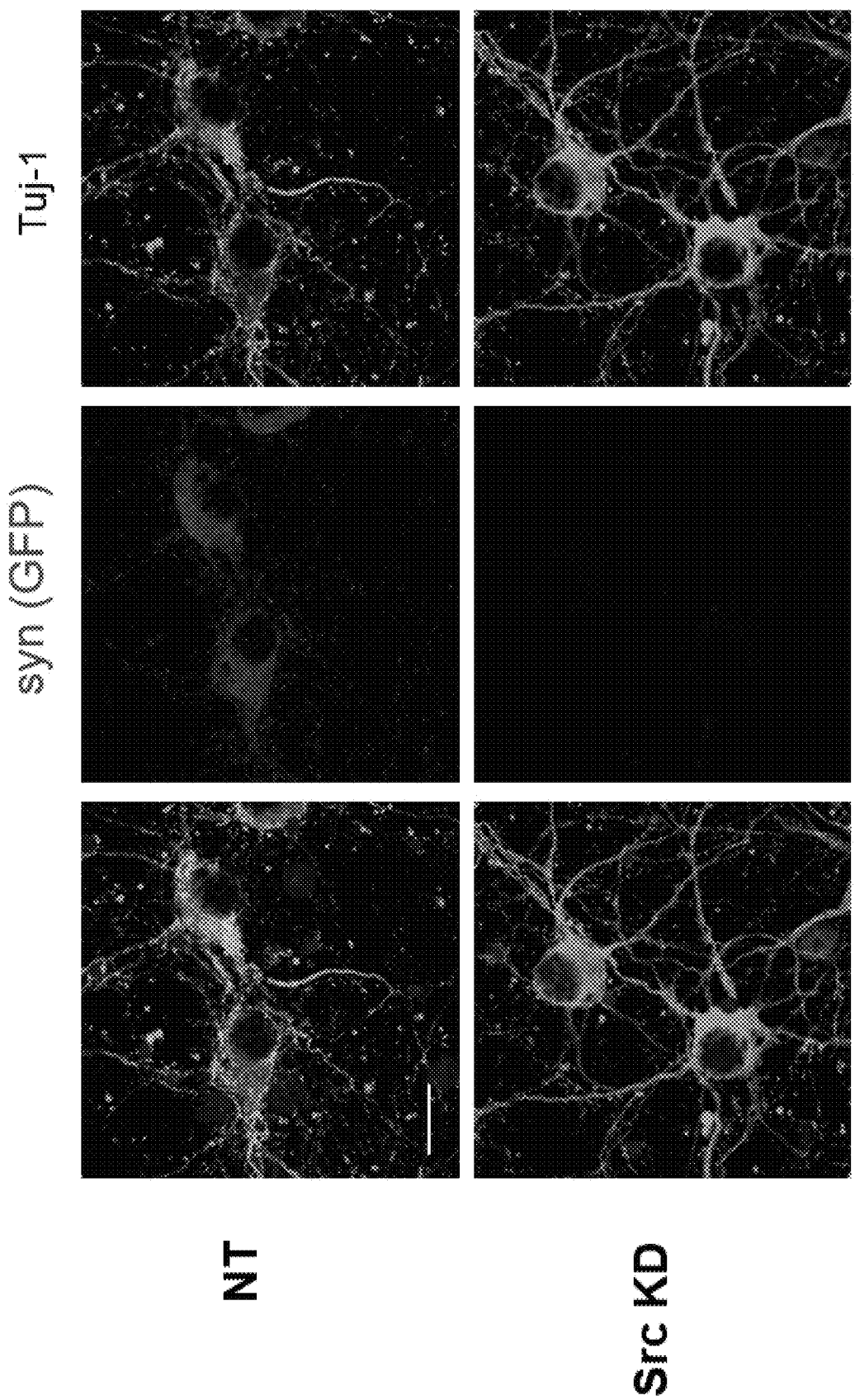
FIG. 11A shows the migration of α-syn when inhibiting the expression of c-src in primary neurons.
Figure 11B:
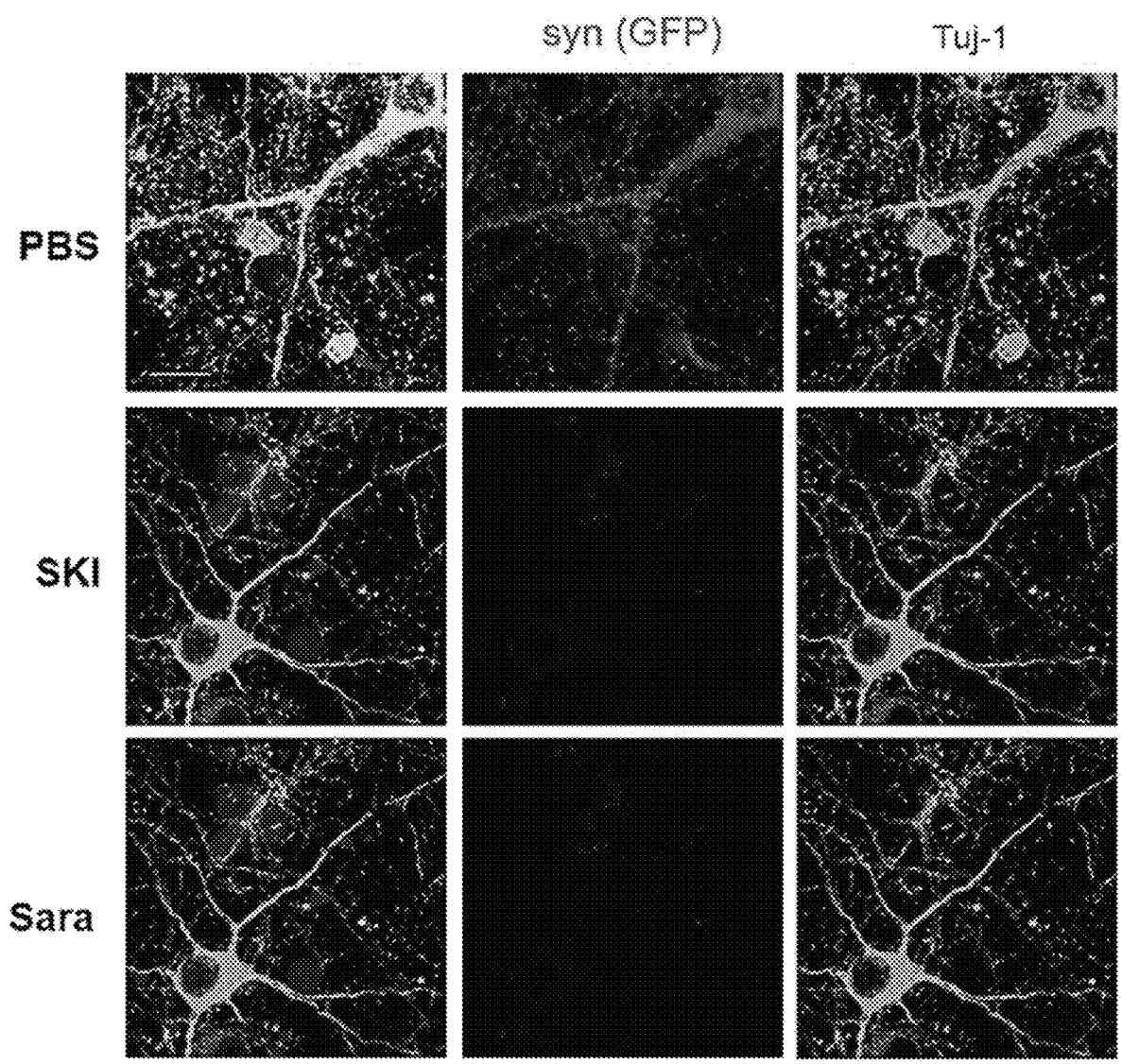
FIG. 11B shows the migration of α-syn when treating primary neurons with a c-src inhibitor.

The result showed that, when the expression of c-src was inhibited using lentivirus in primary neuron culture, the migration of α-syn was reduced (FIG. 11A). In addition, it was found that treatment with the c-src inhibitor reduced the migration of α-syn (FIG. 11B).

Example 10: Effect on the Degree of c-Src Activation on α-Syn Migration

After overexpressing mock, WT c-src GFP, CA (Y527F, kinase active mutant form) c-src GFP or DA (K295F, kinase death mutant form) c-src GFP in SHSY5Y, the degree to which α-syn migrated was determined.

Figure 12:
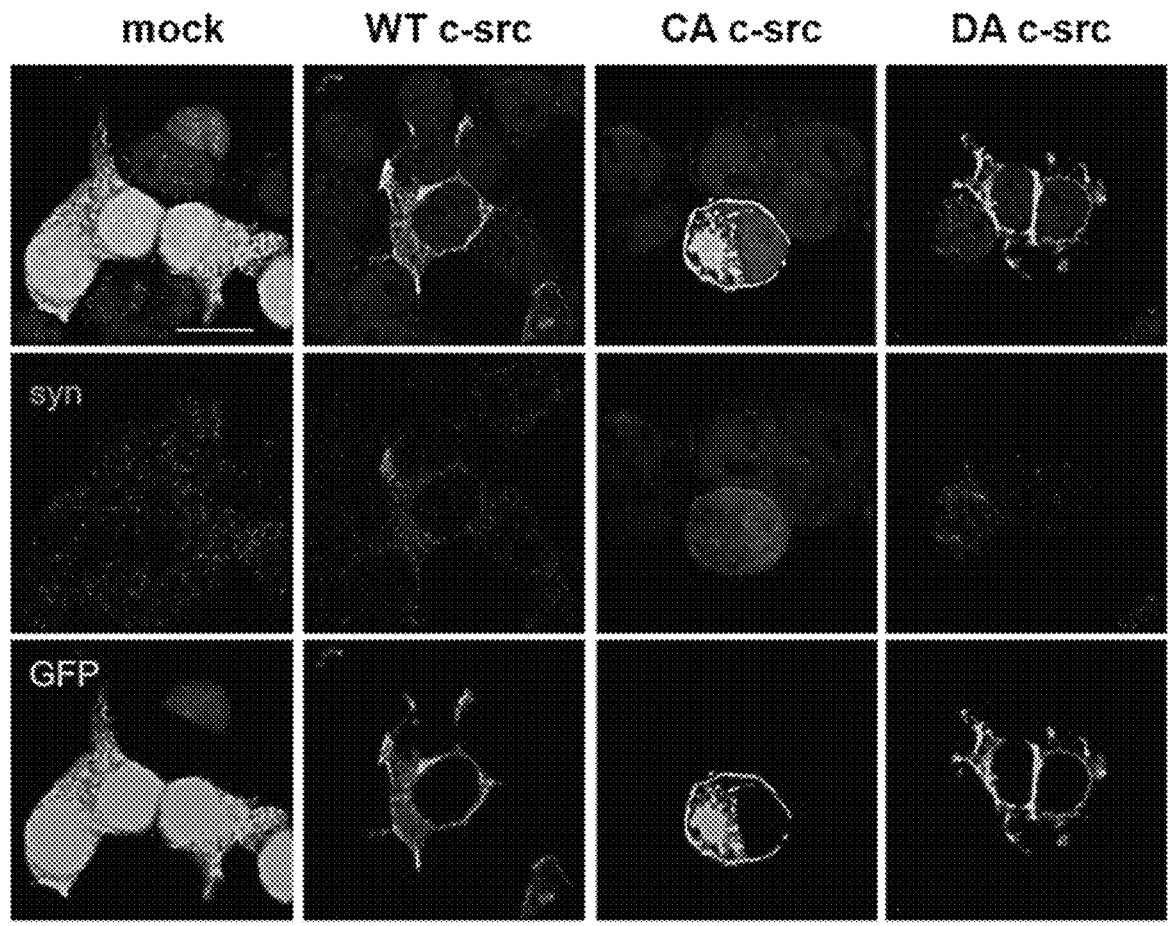
FIG. 12 shows the migration of α-syn depending on the degree of activation of c-src.
Figure 12:
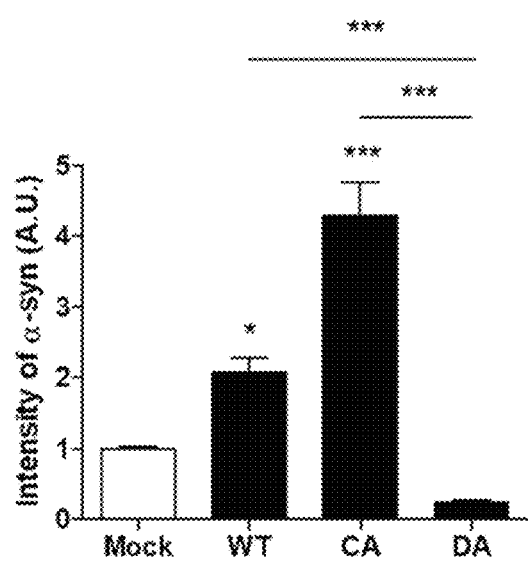

The result showed that the degree of α-syn migration was increased in cells overexpressing WT and CA compared to cells not overexpressing the same (FIG. 12). That is, it was found that the migration of α-syn increased in proportion to the degree of activation of c-src.

INDUSTRIAL APPLICABILITY

The inhibitor for expression or activation of c-src protein of the present invention is capable of inhibiting signaling caused by migration of alpha-synuclein (α-synuclein; α-Syn) to adjacent cells, thus reducing the cytotoxic effect of α-Syn on adjacent cells and inhibiting the denaturation of the monomeric α-syn to aggregated α-syn, which may be a main cause of synucleinopathy, thus being useful as a therapeutic agent for synucleinopathy.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

SEQUENCE LISTING

This application contains a Sequence Listing in ASCII format of 769 bytes, generated on Nov. 30, 2020.

The invention claimed is:

1. A composition for inhibiting aggregation and/or migration of α-syn comprising an inhibitor for expression of a c-src protein, wherein the inhibitor for expression of a c-src protein is a shRNA comprising the nucleotide sequence of SEQ ID NO: 1.

2. A method for treating synucleinopathy in a subject in need thereof, comprising administering an effective amount of a pharmaceutical composition comprising an inhibitor for expression of a c-src protein to the subject, wherein the inhibitor for expression of a c-src protein is a shRNA comprising the nucleotide sequence of SEQ ID NO: 1.

3. The method according to claim 2, wherein the synucleinopathy is Parkinson's disease (PD), dementia with Lewy bodies (DLB) or multiple system atrophy (MSA).

\* \* \* \* \*

```
                         SEQUENCE LISTING

<160> NUMBER OF SEQ ID NOS: 2

<210> SEQ ID NO 1
<211> LENGTH: 58
<212> TYPE: RNA
<213> ORGANISM: Artificial Sequence
<220> FEATURE:
<223> OTHER INFORMATION: shRNA

<400> SEQUENCE: 1
ccgggcucgg cucauugaag acaaucucga gauugucuuc aaugagccga gcuuuuug      58

<210> SEQ ID NO 2
<211> LENGTH: 58
<212> TYPE: RNA
<213> ORGANISM: Artificial Sequence
<220> FEATURE:
<223> OTHER INFORMATION: shRNA

<400> SEQUENCE: 2
ccgggacaga ccugccuuc aagaacucga guucuugaag gacaggucug ucuuuuug       58
```